US012712085B2

(12) United States Patent
Randall et al.

(10) Patent No.: US 12,712,085 B2
(45) Date of Patent: Aug. 18, 2026

(54) GRAPH DATABASE FOR OUTBREAK TRACKING AND MANAGEMENT

(71) Applicants: BAXTER INTERNATIONAL INC., Deerfield, IL (US); BAXTER HEALTHCARE SA, Glattpark (CH)

(72) Inventors: Paul Randall, Gloucester (GB); Ian Smith, Blackburn (GB); Jonathan Haynes, Gloucester (GB); Sam Wilkinson, Gloucester (GB)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 198 days.

(21) Appl. No.: 18/641,806

(22) Filed: Apr. 22, 2024

(65) Prior Publication Data

US 2024/0273101 A1 Aug. 15, 2024

Related U.S. Application Data

(63) Continuation of application No. 17/986,332, filed on Nov. 14, 2022, now Pat. No. 11,966,397, which is a (Continued)

(51) Int. Cl.
*G16H 50/80* (2018.01)
*G06F 3/0484* (2022.01)
(Continued)

(52) U.S. Cl.
CPC .......... *G16H 50/80* (2018.01); *G06F 3/0484* (2013.01); *G06F 16/2455* (2019.01);
(Continued)

(58) Field of Classification Search
CPC ..................................................... G16H 50/80
See application file for complete search history.

(56) References Cited

U.S. PATENT DOCUMENTS

2008/0306896 A1 12/2008 Dash
2018/0052954 A1* 2/2018 Kamalakaran ......... G16H 10/60
(Continued)

OTHER PUBLICATIONS

IPRP for PCT/US2019/040349 mailing date Aug. 4, 2020—22 pages.
(Continued)

*Primary Examiner* — Di Xiao
(74) *Attorney, Agent, or Firm* — K&L Gates LLP

(57) ABSTRACT

A graph database for outbreak tracking and management is disclosed. In an example embodiment, an outbreak management system includes a memory device storing instructions that define a graph database for disease outbreak tracking. The instructions specify for a given host that a host node is created and an episode node is connected to the host node via a 'case' link. The episode node is associated with episode parameters that are related to a disease classification of the host. In addition, the instructions specify that an outbreak node is connected to the episode node via a 'part of' link to indicate that the host has become part of an outbreak of the disease. The outbreak node is connected to a definition node via a 'defined as' link. The definition node specifies disease parameters of the disease for outbreak tracking.

20 Claims, 21 Drawing Sheets

Related U.S. Application Data continuation of application No. 17/335,752, filed on Jun. 1, 2021, now Pat. No. 11,500,872, which is a continuation of application No. 16/460,335, filed on Jul. 2, 2019, now Pat. No. 11,023,467.

(60) Provisional application No. 62/693,017, filed on Jul. 2, 2018.

(51) Int. Cl.

| | |
|---|---|
| ***G06F 16/2455*** | (2019.01) |
| ***G06F 16/901*** | (2019.01) |
| ***G06T 11/26*** | (2026.01) |
| ***G16H 10/60*** | (2018.01) |
| ***G16H 70/60*** | (2018.01) |
| ***H04L 67/10*** | (2022.01) |

(52) U.S. Cl.

CPC .......... *G06F 16/9024* (2019.01); *G06T 11/26* (2026.01); *G16H 10/60* (2018.01); *G16H 70/60* (2018.01); *H04L 67/10* (2013.01); *G06T 2200/24* (2013.01)

(56) References Cited

U.S. PATENT DOCUMENTS

| | | | | |
|---|---|---|---|---|
| 2018/0314793 | A1* | 11/2018 | Gross ..................... | G16B 30/00 |
| 2019/0311810 | A1* | 10/2019 | Sevenster .............. | G06N 5/022 |

OTHER PUBLICATIONS

Safaei et al., “A suitable data model for HIV infection and epidemic detection”, Journal of Occupational Heath and Epidemiology, vol. 4, No. 1 Oct. 2015 pp. 229-240, XP055627476.

Lee Sangkeum et al: “Table2Graph: A Scalable Graph Construction from Relational Tables Using Map-Reduce”, 2015 EEE first International Conference on Big Data Computing Service and Applications, IEEE, Mar. 30, 2015, pp. e94-e301, XP033192915.

Search Report PCT/US2019/040349—mailed date Oct. 14, 2019—5 pages.

Written Opinion PCT/US2019/040349 / mailing date Oct. 14, 2019—11 pages.

Australian Examination Report—Application No. 2019299442 dated Feb. 29, 2024—4 pages.

* cited by examiner

600

Influenza in Gloucester Winter

Background

Time and Place

Clinical Criteria

Any person with at least one of the following clinical forms:

Influenza-like illness (ILI)

- Sudden onset of symptoms

AND at least one of the following four systemic symptoms:

- Fever or feverishness
- Malaise
- Headache
- Myalgia

AND at least one of the following three respiratory symptoms:

- Cough
- Sore throat
- Shortness of breath

Acute respiratory infection (ARI)

- Sudden onset of symptoms

AND at least one of the following four respiratory symptoms:

- Cough
- Sore throat
- Shortness of breath
- Coryza

AND a clinician's judgement that the illness is due to an infection

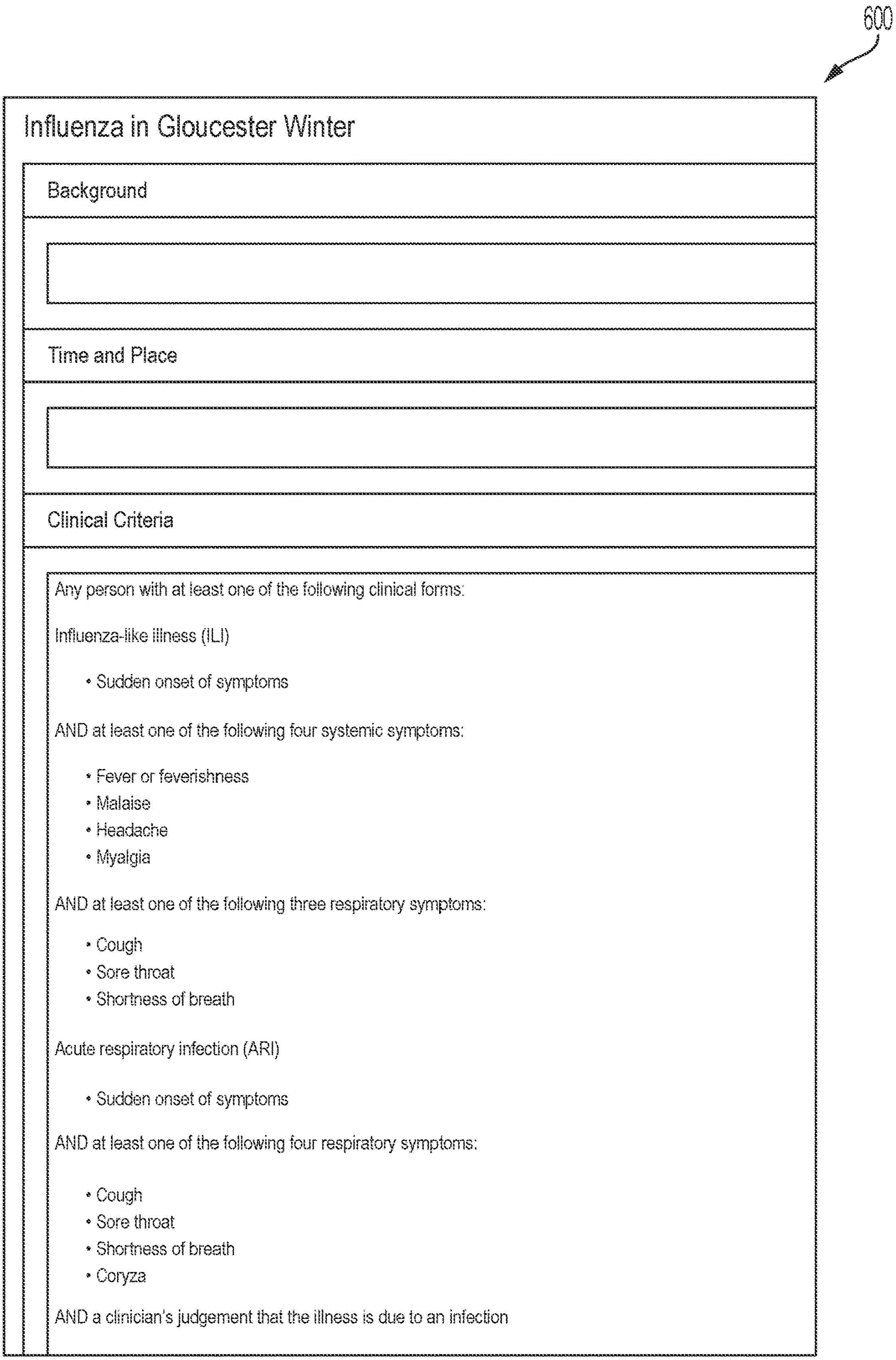

FIG. 6

Laboratory Criteria for Diagnosis

At least one the following four:

- Isolation of influenza virus from a clinical specimen
- Detection of influenza virus nucleci acid in a clinical specimen
- Identification of influenza virus antigen by DFA test in a clinical specimen
- Influenza specific antibody response Sub typing of the influenza isolate should be performed, if possible.

Epidemiological Criteria

Primary mode of transmission

Person-to-person contact

Other modes of transmission

Case Classification

POSSIBLE CASE

Any person meeting the clinical criteria (ILI or ARI)

PROBABLE CASE

Any person meeting the clinical criteria (ILI or ARI) and with an epidemiological link

CONFIRMED CASE

Any person meeting the clinical (ILI or ARI) and the laboratory criteria

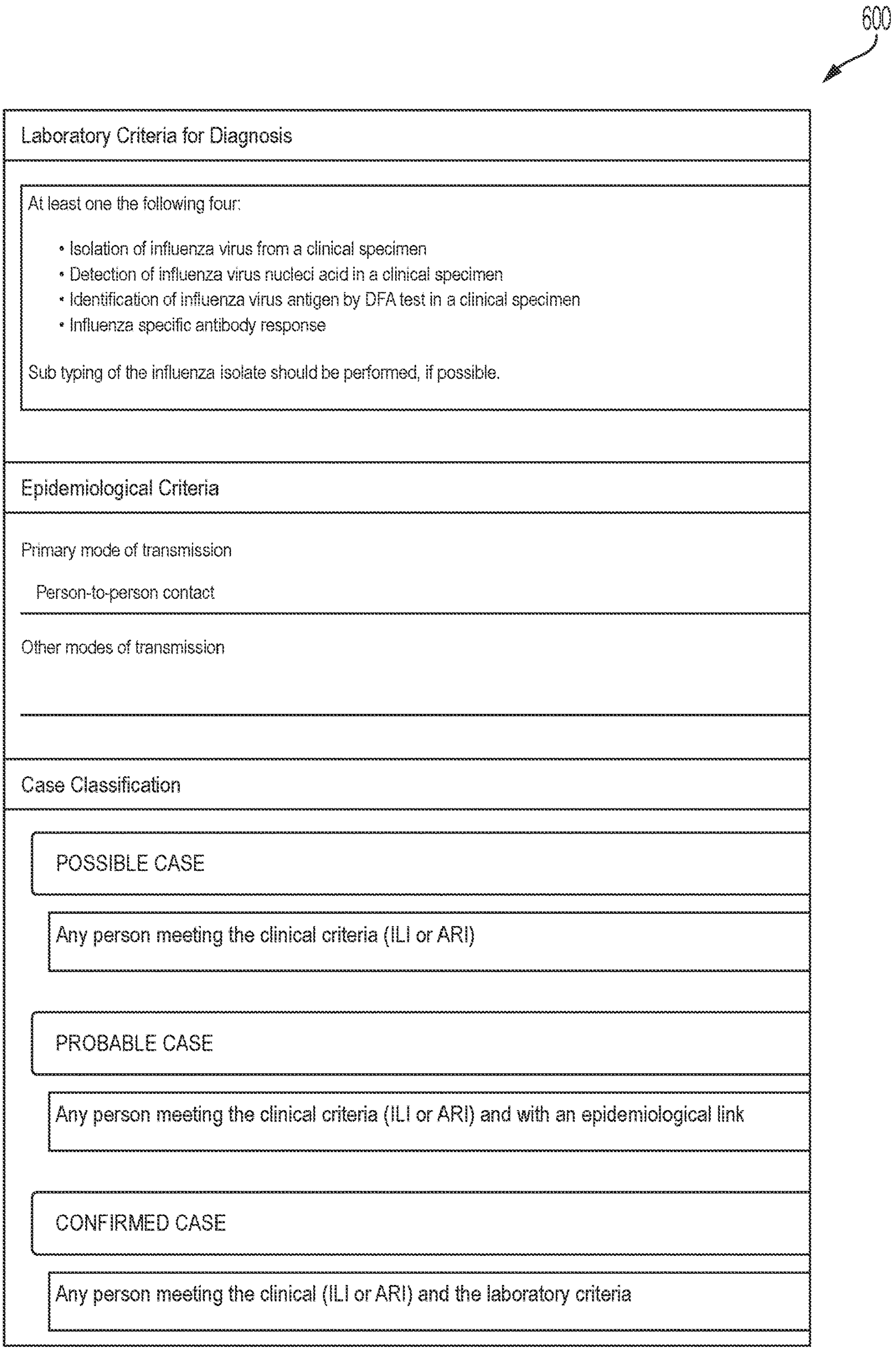

Outbreaks
Norovirus Outbreak in Chantilly Hospital January
Help
Log out
TOOLS
SETS
0
5
10
15
20
25
30
35
40
45
50
1
2
3
4
Outbreak Declared
15-Nov-2018
1
3
5
8
12
15
22
39
43
22
18
5
2
1
12-Nov-18
13-Nov-18
14-Nov-18
15-Nov-18
16-Nov-18
17-Nov-18
18-Nov-18
19-Nov-18
20-Nov-18
21-Nov-18
22-Nov-18
23-Nov-18
24-Nov-18
25-Nov-18

1700

GRAPH DATABASE FOR OUTBREAK TRACKING AND MANAGEMENT

PRIORITY CLAIM

This application claims priority to and the benefit as a continuation application of U.S. patent application Ser. No. 17/986,332, filed Nov. 14, 2022, now U.S. Pat. No. 11,966,397, which is a continuation application of U.S. patent application Ser. No. 17/335,752, filed Jun. 1, 2021, now U.S. Pat. No. 11,500,872, which is a continuation application of U.S. patent application Ser. No. 16/460,335, filed Jul. 2, 2019, now U.S. Pat. No. 11,023,467, which is a non-provisional application of U.S. Provisional Patent Application No. 62/693,017, filed Jul. 2, 2018, the entire contents of which are hereby incorporated by reference and relied upon.

BACKGROUND

As of spring 2018, the world population was approximately 7.6 billion people. The Unit Nations estimates that the population will reach 8 billion by 2024 and 9 billion by 2042. As the world's population increases, the population is relocating to more dense suburban and urban areas in addition to encroaching upon undeveloped areas, such as forests and grasslands. For example, the city of Manila in the Philippines has a density of 107,000 people per square mile while more populous Indian cities, such as Mumbai have almost 12 million people with an average density of 73,000 people per square mile.

In addition to the population increasing and becoming denser, travel, such as airline travel, is becoming more commoditized, enabling more people to travel further distances. Increasing wages among the world's middle class enables more of the world's population to travel regionally, nationally, or internationally. Globalization of business and trade further increases daily foreign contacts. Altogether, increased populations living in dense areas combined with an increasing mobile population creates optimal conditions for the rapid spread of contagions and other outbreaks. Indeed, the world has had a number of scares the past few years including severe acute respiratory syndrome ("SARS"), swine flu, and Ebola, not to mention the human immunodeficiency virus ("HIV"). The Center for Disease Control and Prevention ("CDC") evens maintains a website of currently recognized outbreaks in the United States and worldwide.

While the world advances, the tracking and management of outbreaks lags behind. Oftentimes, it takes disease researchers months to identify an outbreak and even longer to determine its distribution, spread, and origin. Generally, infection tracking is a manual process that involves studying medical records, government records, and field notes. Some government organizations and large medical centers build and analyze relational databases of outbreak information to determine distribution, spread, and origin. However, extensive effort is needed to input the correct data. Additionally, significant computational power is needed to analyze the collected data. As a result of the effort and power needed, only relatively severe or harmful outbreaks are tracked, leaving many outbreaks untracked.

In addition to above, medical data related to an outbreak is only entered after an outbreak has been identified. The lag between the outbreak occurring, identification, data gathering, and analysis can result in an outbreak quickly expanding before much is known. As many healthcare professionals believe, the next pandemic (or wave of pandemics) will begin small, in isolated areas such as urban centers or on the fringes of developed areas, and proceed under health radars until a significant portion of the world's population is affected.

SUMMARY

The present disclosure sets forth a graph database for outbreak tracking and management. In particular, the disclosure describes a method, system, and apparatus for the creation and updating of a graph database to track one or more outbreaks. The method, system, and apparatus disclosed herein may also be configured to analyze the graph database to provide for outbreak management and outbreak predictions. The graph databases incorporate medical, positional, temporal, and/or demographic relationships between nodes according to a predefined structure. The definitions and relationships provided among different types of nodes enables information to automatically be incorporated into the graph database. Further, the definitions and relationships enable an origin of an outbreak to be located for identifying a cause and potential solutions for an outbreak.

Aspects of the subject matter described herein may be useful alone or in combination with one or more other aspect described herein. Without limiting the foregoing description, in a first aspect of the present disclosure, an outbreak management server apparatus includes an interface to receive patient data related to patients and a node processor communicatively coupled to the interface and configured to create an outbreak tracking graph database. The node processor creates the outbreak tracking graph database by comparing the patient data to disease parameters of different diseases, the disease parameters specifying conditions for a 'possible' classification for the respective disease, a 'probable' classification for the respective disease, and a 'confirmed' classification for the respective disease. For each patient in which at least one of the 'possible', 'probable', and 'confirmed' classification is determined for one of the diseases, the node processor adds the patient to the graph database that is associated with an outbreak of the determined disease by creating a host node for the patient, creating an episode node that is connected to the host node via a 'case' link, the episode node being associated with episode parameters that are related to the disease classification of the host, and creating an outbreak node that is connected to the episode node via a 'part of' link to indicate that the host has become part of the outbreak for the determined disease, the outbreak node being connected to a definition node via a 'defined as' link, the definition node specifying the disease parameters of the disease that is related to the outbreak node. The outbreak management server apparatus also includes a database analyzer configured to analyze the graph database that is associated with the outbreak of the determined disease to display for identification at least one of an index patient or relationships among the patients.

In accordance with a second aspect of the present disclosure, which may be used in combination with any other aspect listed herein unless stated otherwise, the node processor is configured to use at least a portion of the patient data to create epidemiological links between at least some of the host nodes that are linked to the same outbreak node.

In accordance with a third aspect of the present disclosure, which may be used in combination with any other aspect listed herein unless stated otherwise, the database analyzer is configured to receive a request, from a user device, to view relationships of a designated host that is associated with a particular disease that is specified by a related outbreak node, determine epidemiological links between the designated host and at least one of (i) other hosts that are connected to the same related outbreak node, or (ii) persons that have been in a same location at the same time as the host, and cause a user interface to be displayed on the user device that graphically shows the designated host connected to the other hosts to show potential contacts that are at risk of contacting the particular disease that is associated with the host.

In accordance with a fourth aspect of the present disclosure, which may be used in combination with any other aspect listed herein unless stated otherwise, the node processor is configured to determine the ‘possible’, ‘probable’, or ‘confirmed’ classification for at least some of the other hosts, and the database analyzer is configured to provide a graphical indication of the ‘possible’, ‘probable’, or ‘confirmed’ classification in the user interface for the at least some of the other hosts.

In accordance with a fifth aspect of the present disclosure, which may be used in combination with any other aspect listed herein unless stated otherwise, the epidemiological links include at least one of an ‘airborne’ link, an ‘animal reservoir’ link, an ‘environmental reservoir’ link, a ‘food and drinking water’ link, an ‘insect bite’ link, an ‘animal-to-person contact’ link, a ‘contaminated object’ link, a ‘droplet spread’ link, or a ‘person-to-person contact’ link, and each of the other hosts are at least one of a patient, a clinician, a person, an animal, a fomite, or an object.

In accordance with a sixth aspect of the present disclosure, which may be used in combination with any other aspect listed herein unless stated otherwise, the node processor is configured to, for each host node in which specimen data is available within the patient data for the respective patient create a specimen node that is linked to the respective host node via a specimen link, the specimen node being associated with specimen parameters that indicate a time or status of a specimen acquired from the patient, create an isolate node that is linked to the specimen node via an isolate link, the isolate node being associated with isolate parameters that specify an isolate in specimen results that are related to the acquired specimen, and create an organism node that is linked to the isolate node via an organism link, the organism node being associated with organism parameters that specify at least one organism that was found in an isolation routine.

In accordance with a seventh aspect of the present disclosure, which may be used in combination with any other aspect listed herein unless stated otherwise, the node processor is configured to determine, as a first set of hosts, hosts that have the same organism specified in the respective organism parameter of the organism node, determine as a second set of hosts from the first set of hosts, hosts that are linked to the same outbreak node, and display a graphical representation that shows connections between the organism node and the outbreak node for the second set of hosts to show a spread of the disease and a biologic that is responsible for the outbreak of the disease.

In accordance with an eighth aspect of the present disclosure, which may be used in combination with any other aspect listed herein unless stated otherwise, the node processor is configured to, for each host node in which location data is available within the patient data for the respective patient create a stay node that is linked to the respective host node via a stayed link, the stay node being associated with stay parameters that specify a date/time that the host node was in a particular location, and create a location node that is linked to the stay node via an ‘in’ link, the location node being associated with location parameters that specify the particular location.

In accordance with a ninth aspect of the present disclosure, which may be used in combination with any other aspect listed herein unless stated otherwise, the particular location includes at least one of a hospital bed identifier or node, a room identifier or node, a corridor identifier or node, a ward identifier or node, a level identifier or node, a wing identifier or node, a hospital identifier or node, a structure identifier or node, a building identifier or node, a street identifier or node, a site identifier or node, an area identifier or node, a state identifier or node, a country identifier or node, or GPS coordinates.

In accordance with a tenth aspect of the present disclosure, which may be used in combination with any other aspect listed herein unless stated otherwise, the interface is configured to receive the patient data from at least one of an Electronic Medical Record (“EMR”) server or a third-party server, and wherein the patient data includes at least one of patient medical data, social media data, location data, or demographic data.

In accordance with an eleventh aspect of the present disclosure, which may be used in combination with any other aspect listed herein unless stated otherwise, an outbreak management system comprises a memory device storing instructions therein, the instructions defining a graph database for disease outbreak tracking. The instructions specify for a given host that a host node is created, the host node being associated with host parameters, an episode node is connected to the host node via a ‘case’ link, the episode node being associated with episode parameters that are related to a disease classification of the host, and an outbreak node is connected to the episode node via a ‘part of’ link to indicate that the host has become part of an outbreak of the disease, the outbreak node being connected to a definition node via a ‘defined as’ link, the definition node specifying disease parameters of the disease that is related to the outbreak node. The system also includes an outbreak management server configured to receive patient data related to the host, and store at least some of the received patient data to the graph database at one or more parameters of at least one of the host node, the episode node, or the outbreak node based on contents of the at least some of the received patient data matching parameter definitions of the respective node.

In accordance with a twelfth aspect of the present disclosure, which may be used in combination with any other aspect listed herein unless stated otherwise, the server is configured to connect the host node to the outbreak node via the episode node after determining at least some of the patient data matches at least some of the disease parameters of the definition node.

In accordance with a thirteenth aspect of the present disclosure, which may be used in combination with any other aspect listed herein unless stated otherwise, the host parameters include at least one of a name of the host, a patient classification flag, a clinician classification flag, a person classification flag, an animal classification flag, a fomite classification flag, an object classification flag, patient demographic data, or patient medical data.

In accordance with a fourteenth aspect of the present disclosure, which may be used in combination with any other aspect listed herein unless stated otherwise, the episode parameters include at least one of a case number for the host, a ‘possible’ classification for the disease for the host, a ‘probable’ classification for the disease for the host, a ‘confirmed’ classification for the disease for the host, an immunization status of the host, an immunization type of the host, a flag indicative that the host acquired the disease in a medical facility, or death information related to the host.

In accordance with a fifteenth aspect of the present disclosure, which may be used in combination with any other aspect listed herein unless stated otherwise, the disease parameters include at least one of a name of the disease, a background of the disease, a time/place related to the disease, clinical criteria for the disease, laboratory criteria for the disease, modes of transmission for the disease, criteria for determining the 'suspected' classification, criteria for determining the 'probable' classification, and criteria for determining the 'confirmed' classification.

In accordance with a sixteenth aspect of the present disclosure, which may be used in combination with any other aspect listed herein unless stated otherwise, the server is configured to determine a case classification for the episode node for the host node by comparing at least some of the patient parameters to the criteria for determining the 'suspected', 'probable', and 'confirmed' classifications in the disease parameters, and store at the respective episode parameter of the episode node at least one of the 'suspected', 'probable', or 'confirmed' classification for the disease based on the comparison.

In accordance with a seventeenth aspect of the present disclosure, which may be used in combination with any other aspect listed herein unless stated otherwise, the server is configured to generate the case number for the respective episode parameter of the episode node after determining the 'confirmed' or 'probable' classification for the host.

In accordance with an eighteenth aspect of the present disclosure, which may be used in combination with any other aspect listed herein unless stated otherwise, the instructions specify for the given host that a role node is connected to the episode node via a role link, the role node being associated with role parameters that specify whether the host is a patient, a clinician, a family member, or an individual.

In accordance with a nineteenth aspect of the present disclosure, which may be used in combination with any other aspect listed herein unless stated otherwise, the instructions specify for the given host that a symptom node is connected to the host node via a 'has symptom' link, the symptom node being associated with one or more symptom parameters that specify at least one of a start date of a symptom, an end date of a symptom, and a symptom identifier corresponding to a symptom experienced by the host.

In accordance with a twentieth aspect of the present disclosure, which may be used in combination with any other aspect listed herein unless stated otherwise, the instructions specify for the given host that the host node is connected to another host node via an epidemiological link, and the epidemiological link includes at least one of an 'airborne' link, an 'animal reservoir' link, an 'environmental reservoir' link, a 'food and drinking water' link, an 'insect bite' link, an 'animal-to-person contact' link, a 'contaminated object' link, a 'droplet spread' link, or a 'person-to-person contact' link.

In accordance with a twenty-first aspect of the present disclosure, any of the structure and functionality illustrated and described in connection with FIGS. 1 to 20 may be used in combination with any of the structure and functionality illustrated and described in connection with any of the other of FIGS. 1 to 20 and with any one or more of the preceding aspects.

In light of the aspects above and the disclosure herein, it is accordingly an advantage of the present disclosure to provide graph database that provides for the tracking and management of outbreaks.

It is another advantage of the present disclosure to provide a system that creates graphs databases according to a predefined data structure to enable a source of an outbreak to be determined.

It is another advantage of the present disclosure to provide a system that creates graphs databases according to a predefined data structure to identify potential or susceptible individuals to an outbreak.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIGS. 6 and 7 show diagrams of graphical representations of outbreak conditions, according to example embodiments of the present disclosure.

DETAILED DESCRIPTION

Figure 1:
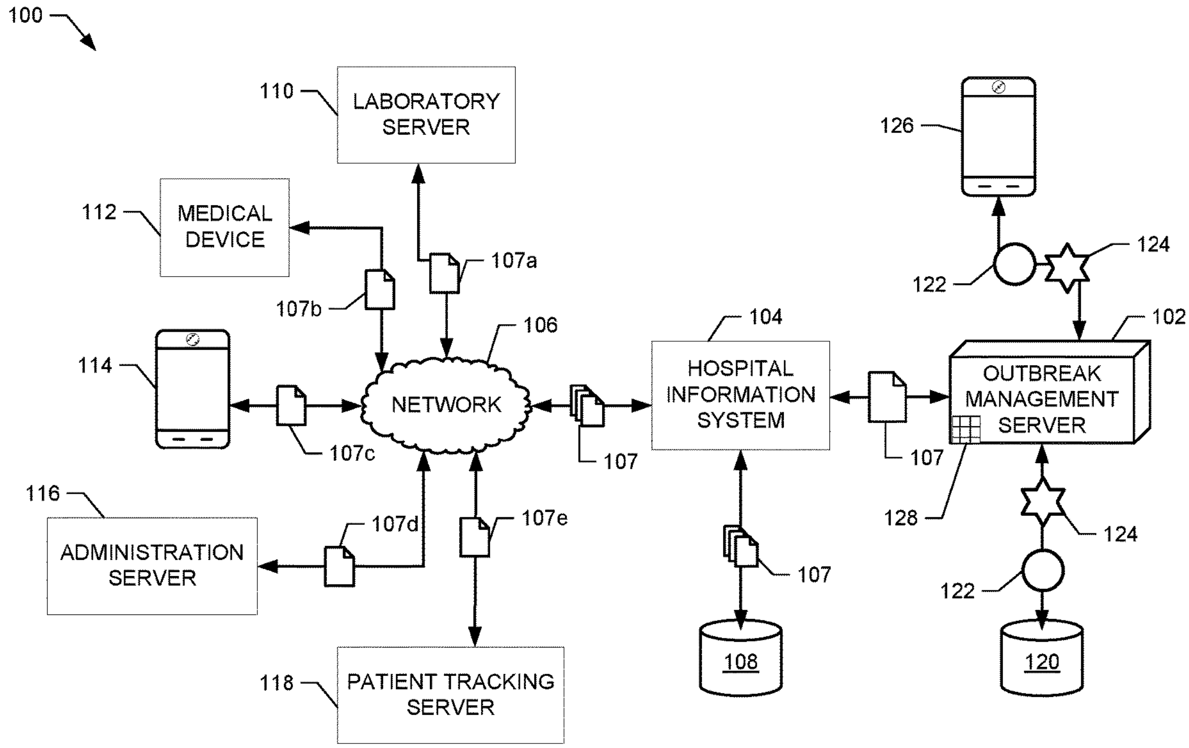
FIGS. 1 to 3 show example embodiments of an example outbreak tracking and management system including an outbreak management server, according to example embodiments of the present disclosure.

The present disclosure relates in general to a method, system, and apparatus that create and analyze outbreak graph databases for outbreak management. The graph databases disclosed herein are specifically configured to provide a medical, positional, and/or temporal relationship between components of an outbreak. The unique definition between the components of the graph database enable links to be automatically determined among a plurality of individuals with minimal input from clinicians. The example method, system, and apparatus disclosed herein are configured to perform certain defined analytics on the graph database to determine, in near real-time, distribution, spread, and origin of an outbreak as soon as a first suspected, probable or confirmed case is received.

In comparison to graph databases, traditional relational databases comprise tables of data. Unique keys are used to link certain data together from different tables. Relational databases are generally adapted for flat data layouts where relationships between data are only one to three levels deep. As additional data levels are added or data becomes increasing interrelated, relational databases require significant computational power for analysis. Some computation may be avoided using indexes with relational databases. However, the indexes may be stale as new data is added, which may require recompilation of the databases and subsequent analysis.

As disclosed herein, the methods, apparatus, and system are configured to operate with graph databases for outbreak management. A graph database includes a data structure that links nodes via a data relationship (e.g., an edge). The relationships between nodes may be semantic, which enable semantic analysis and queries to be conducted. Each of the nodes may have one or more parameters or attributes that define and store underlying data. The example graph database disclosed herein enables complex hierarchical structures to be computationally efficiently modeled and constantly updated as new data is provided. In some instances, the disclosed graph databases may have seven to twenty different data levels. Graph databases are especially well adapted for outbreak management since the hierarchical multi-level nature of a graph database approximates the actual spread of a condition during an outbreak.

The graph database disclosed herein includes nodes and edges/relationships. The graph database is configured to relate data items in a memory or store to a collection of nodes and edges. In some embodiments, the nodes and edges may be stored in a table or list, with edges being used to link nodes together. The edges of a graph database enable stored data to be linked together and retrieved with one or a few operations. In the illustrated example, a node represents an outbreak, a definition of an outbreak, an episode of an outbreak, a host (e.g., a person, object, an animal, equipment, a fomite, etc.), a symptom of a host, a location of a host, a date/time a host was at a location, and a location hierarchy (e.g., organizational structure of a hospital facility). Each node has one or more parameters or attributes, which define stored data that is relevant to the node. Nodes also include edges or relationships. The edges or relationships connect nodes together and define the relation between them.

The example graph databases created and processed by the example methods, apparatus, and system may be stored in a data structure configured for storing nodes, parameters or attributes, and relationships. In some embodiments, the graph database may be configured for a query language such as Gremlin, SPARQL, Cypher, etc. In other embodiments, the graph database may be accessed via one or more application programming interfaces ("APIs").

The example graph databases disclosed herein enable outbreak information to be created automatically from patient medical records, demographic databases, and/or clinician entry information. As such, the graph databases enable outbreaks to be tracked for each person identified as having a defined condition. As additional information is received, the example system, methods, and apparatus are configured to update, in near-real time, the graph database to provide an up-to-date representation of potential and actual outbreaks. Additional information is easily added by the example system, methods, and apparatus as through the creation of nodes, parameters or attributes, and/or relationships. Since the new nodes, parameters or attributes, and relationships build on what is already in the graph database, re-compilation of the database is not needed.

The example system, method, and apparatus disclosed herein are configured to analyze the graph databases to determine the distribution, spread, and origin of an outbreak in addition to providing information to help stop the spread. For example, the system, method, and apparatus disclosed herein may be configured to identify 'at risk' persons for quarantine or vaccination, provide graphical representations to illustrate the progress of an outbreak, identify points of intervention, provide reports to governmental bodies, conduct statistical analysis of outbreaks to determine for example, attack rates, epicurves, etc., and/or combine outbreak data to determine an overall picture of a burden of an outbreak on a health system region, or country.

The example system, method, and apparatus disclosed herein are configured to create and manage different types of outbreaks. As disclosed herein, outbreaks may include small public health incidents (e.g., food poisoning) and/or large public health incidents (e.g., epidemics or pandemics). Outbreaks may also include traumatic neurological events, contamination events, and/or hospital-based contagion infections. As such, outbreaks are not limited to viral or bacterial infections, but can also include chemical, radiation, or biological exposures.

I. Outbreak Tracking and Management System Embodiments

Figure 2:
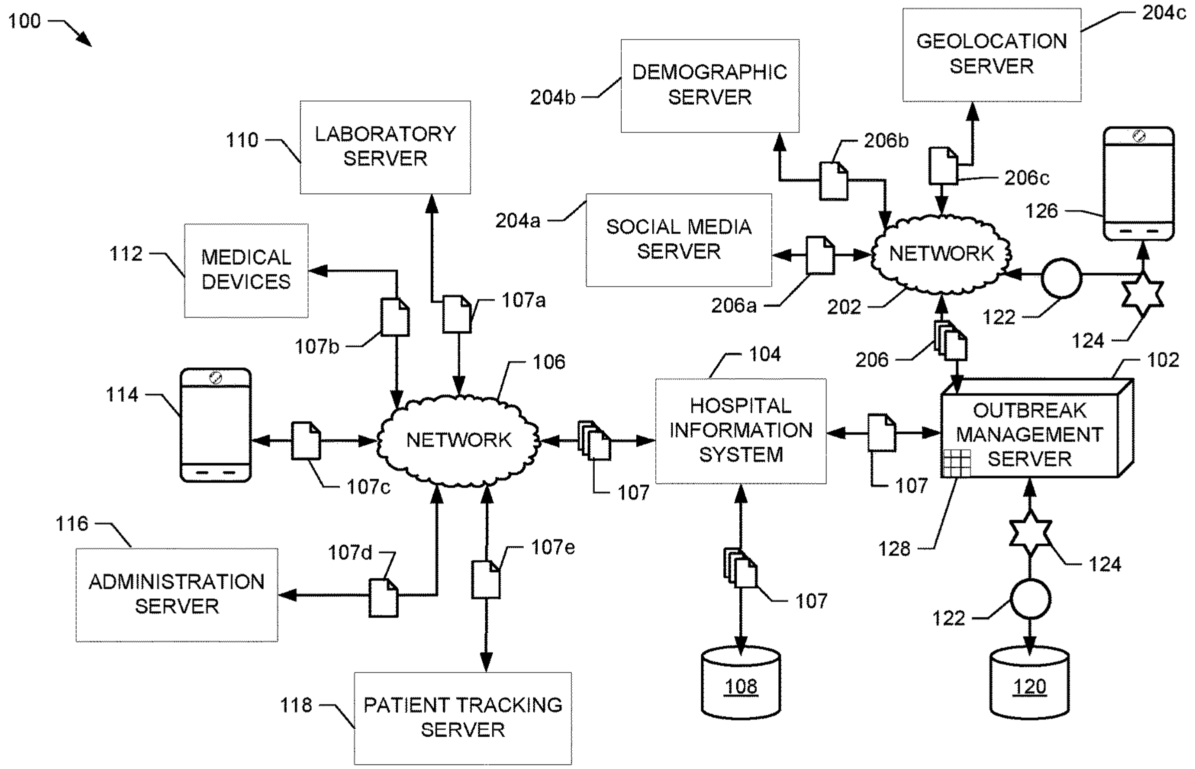
Figure 3:
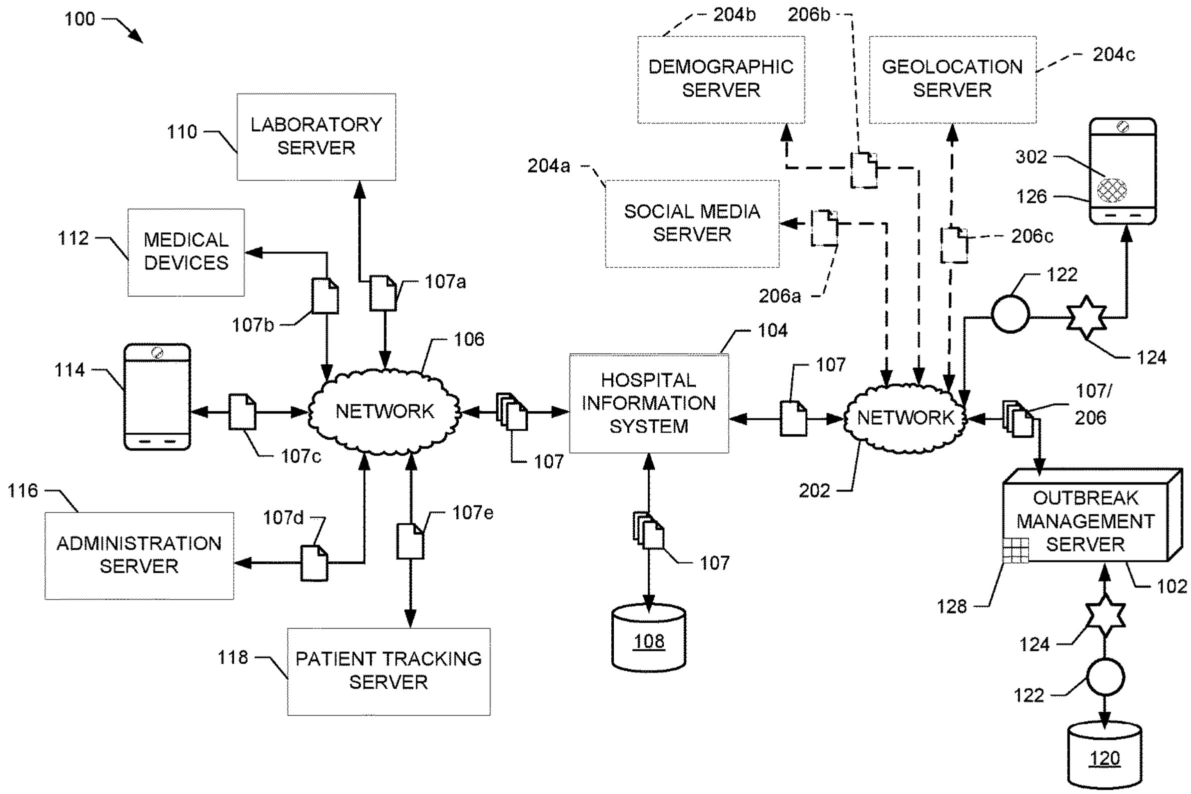

FIGS. 1 to 3 show example embodiments of an example outbreak tracking and management system 100, according to example embodiments of the present disclosure. The example system 100 includes an outbreak management server 102 and a Hospital Information System ("HIS") 104. The server 102 is configured to create, analyze, and manage graph databases. The example HIS 104 is configured to provide connectivity within a hospital or medical environment. In some examples, the server 102 may be included within the HIS 104. In other examples, the server 102 may be external to and communicatively coupled to the HIS 104.

The example HIS 104 is communicatively coupled via a network 106 to one or more devices or computers that are configured to transmit or otherwise provide patient medical data 107. The HIS 104 stores the patient medical data 107 as an Electronic Medical Record ("EMR") within a memory device 108. In the illustrated example, the HIS 104 is communicatively coupled to a laboratory server 110, which is configured to transmit laboratory patient medical data **107*a*, a medical device 112 configured to transmit device patient medical data 107*b*, a clinician device 114 configured to transmit clinician patient medical data 107*c*, an administration server 116 configured to transmit administration patient medical data 107*d*, and a patient tracking server 118 configured to transmit patient tracking medical data 107*c***.

The laboratory server 110 may be communicatively coupled to one or more laboratory instruments that generate laboratory data from analysis of one or more biological samples from a patient. The laboratory server 110 stores the laboratory data as the laboratory patient medical data **107*a*, which is periodically transmitted to the patient's EMR via the HIS 104, which is stored at the memory device 108**.

The medical device 112 includes any type of clinical medical device including an infusion pump, a renal failure therapy machine, a physiological sensor, a patient bedside monitor, a pulse-ox monitor, a CT scanner, an MRI scanner, etc. The medical device 112 generates operational data and/or alarms/alerts regarding a treatment performed on a patient or a measurement performed on a patient. The data is stored as the device patient medical data 107*b* and transmitted to the patient's EMR located at the memory device 108. While the example environment 100 of FIG. 1 shows one medical device, it should be appreciated that the environment 100 may include tens to thousands of medical devices.

The example clinician device 114 includes any smartphone, tablet computer, laptop computer, desktop computer, workstation, etc. that is configured to receive clinician-entered data regarding a condition of a patient. The data may include observation notes, prescriptions, treatments, diagnosis, observed/identified symptoms, etc. The received data is stored as the clinician patient medical data 107*c* and transmitted to the patient's EMR, which is stored at the memory device 108. While the example environment 100 of FIG. 1 shows one clinician device 114, it should be appreciated that the environment 100 may include tens to thousands of devices.

The example administration server 116 is configured to receive patient administration information. The information includes patient demographic and/or physiological information such as gender, weight, age, birth date, height, medical history, etc. The information may also include a ward (e.g., care area) and/or room assigned to the patient. The information may be received at the time of admittance of the patient or entered/acquired after a patient has been admitted or moved to a new location in a medical facility. The administration server 116 transmits the administration information as the administration patient medical data 107*d* to the patient's EMR at the memory device 108.

The example patient tracking server 118 is configured to track a patient's location in a medical facility. The example server 118 is configured to receive information indicative of a ward to which a patient is assigned or has been moved. The server 118 is also configured to receive information indicative of a room or bed to which the patient is assigned. The server 118 transmits the patient tracking medical data 107*e* to the patient's EMR at the memory device 108 via the HIS 104. The server 118 may transmit the data 107*e* each time a patient's location changes, and may include an indication of a discharge.

The example network 106 may include any wired or wireless local area network ("LAN") and/or wide area network ("WAN"). In some examples, the network 106 may include one or more firewalls, gateways, and/or switches that control access, formatting, and data routing. The network 106 may be configured to be self-contained within a medical facility and/or may include an external network and corresponding interfaces/virtual tunnels.

The example HIS 104 is configured to store the received data 107 to the appropriate patient EMR stored in the memory device 108. In some embodiments, the patient medical data 107 includes a patient name or other identifier that corresponds to an identifier within or linked to the EMR. The HIS 104 compares identifiers to determine a match. After a match is identified, the HIS 104 stores the patient medical data to the matching EMR.

Figure 5:
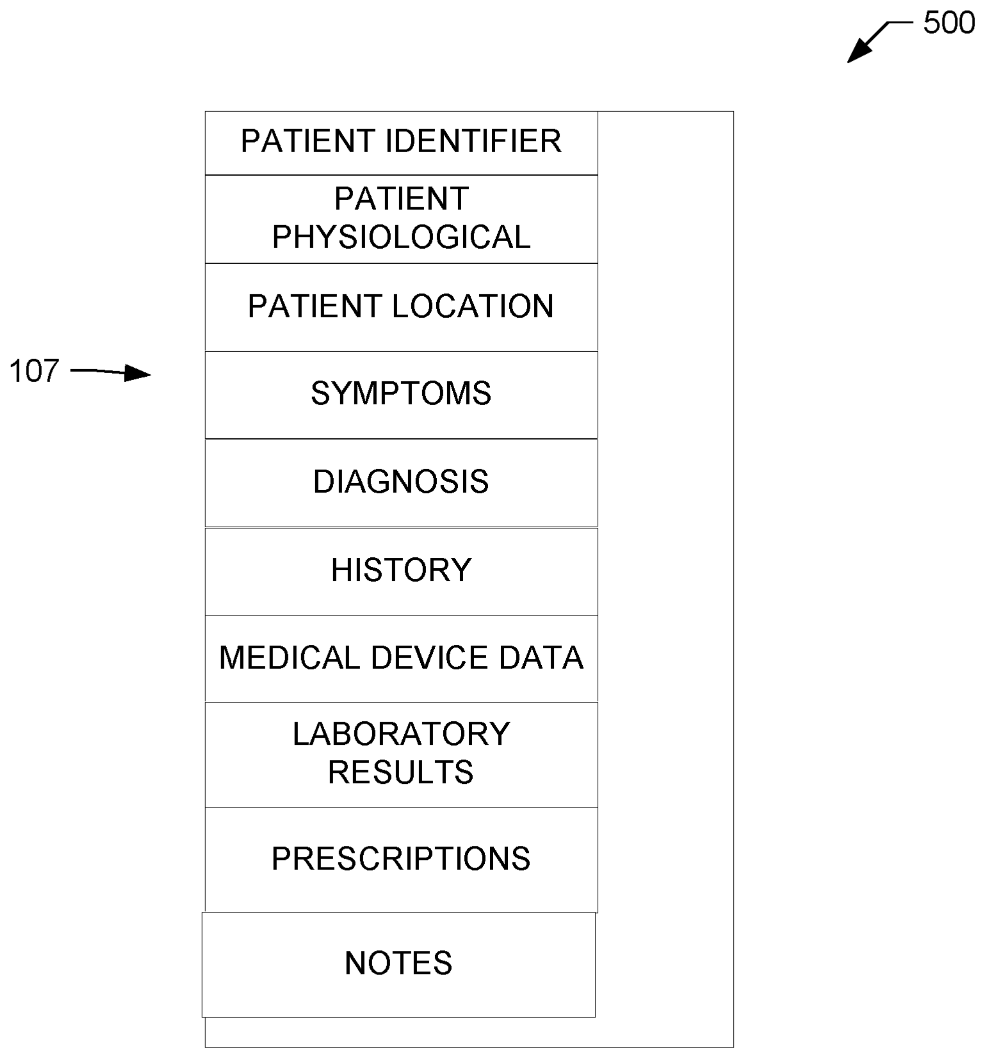
FIG. 5 shows a diagram of an example patient electronic medical record, according to an example embodiment of the present disclosure.

FIG. 5 shows an example patient EMR 500, according to an example embodiment of the present disclosure. The EMR 500 includes patient medical data 107 received from one or more of the devices 110 to 118 of FIG. 1. This includes a patient identifier and/or name, patient physiological and/or demographic information, patient location(s), symptoms, diagnosis, medical history, medical device data, laboratory results, prescriptions, and notes. The patient medical data 107 is stored in a relational or table data structure and provides a substantive medical characterization of a patient. In some examples, the different categories of information include data fields, labels, or metadata that identifies the stored data. For example, the EMR 500 may include a label "room number" next to an alphanumeric value that corresponds to a patient's room and bed. In other embodiments, each of the different types of patient medical data are stored to different fields or sections of the EMR 500 in a predefined or pre-structured arrangement.

Returning to FIG. 1, the example HIS 104 is configured to provide access to the patient EMRs 500 (and more generally the patient medical data 107) that is located in the memory device 108. For example, the clinician device 114 may access the memory device 108 via the HIS 104 to view, edit, add, or remove patient medical data from a patient's EMR. In addition, the example outbreak management server 102 is configured to periodically (e.g., every 60 seconds, every 5 minutes, every hour, etc.) or continuously access the memory device 108 to acquire patient medical data 107. Additionally or alternatively, the HIS 104 may transmit a copy of patient medical data 107 to the outbreak management server 102 at periodic times or as the data is received.

The example outbreak management server 102 is configured to enable clinicians to specify a framework for the creation of outbreak graph databases. The example outbreak management server 102 operates accordingly to the framework to automatically (or with minimal clinician input) create graph databases for specified types of outbreaks. The outbreak management server 102 is also configured to analyze graph databases to determine a distribution, spread, and origin of outbreaks. The management server 102 is configured to render graph databases into a graphical representation to provide different views of an outbreak or provide results of an analysis or semantic query. The outbreak management server 102 may be configured to provide an interactive graphical representation that enable a clinician to filter or hide certain levels of data or view parameter or attribute values of the underlying data for one or more specified nodes.

The outbreak management server 102 is communicatively coupled to a memory device 120, which is configured to store graph databases. As illustrated in FIG. 1, the outbreak management server 102 receives or otherwise accesses copies of patient medial data 107. The outbreak management server 102 is configured to create, from the copy of the patient medical data 107, graph databases 122, including nodes, relationships, and parameters of graph databases. The outbreak management server 102 analyzes the graph databases 122 to create analysis data 124, which is also stored in the memory device 120.

The outbreak management server 102 of FIG. 1 is communicatively coupled to one or more user devices 126 via a wired or wireless network. The server 102 is configured to transmit the graph databases 122 and/or analysis data from the memory device 120 for viewing, navigating, and/or editing at the user device 126. In some embodiments, the user device 126 accesses the outbreak management server 102, which provides and/or transmits an interface for interacting with the graph databases 122 that are located in the memory device 120. The interface is configured to include features that enable a user to submit a semantic query and/or select options for analysis. In response to the request from the user device 126, the example outbreak management server 102 performs the requested analysis on the graph database to generate the analysis data 124, which is sent to the user device 126 for display. The interface may also be configured to enable the user device 126 to modify or add nodes, relationships, and/or parameters to a graph database (or confirm nodes, relationships, and/or parameters).

The example user device 126 includes a smartphone, tablet computer, laptop computer, desktop computer, workstation, server, etc. In some examples, the user device 126 may comprise the clinician device 114. In other examples, the user device 126 may be a device that is external or separate from a hospital system that can connect to the server 102 via a secure gateway, access port, and/or firewall.

In some embodiments, the outbreak management server 102 operates according to instructions 128 stored in a memory (e.g., the memory device 120), which when executed, cause the outbreak management server 102 to perform the operations, steps, methods, procedures, routines, algorithms, etc. described herein. For example, the instructions enable the server 102 to create, manage, and analyze the outbreak graph databases 122 according to user-specified criteria. The example instructions 128 may also be configured to cause the outbreak management server 102 to improve upon how outbreak medical information is structured in a database by creating a storage structure or framework based on nodes and relationships that approximates actual outbreaks. The instructions 128 specify the creation of outbreak graph databases with well defined relationships between different types of nodes at different data levels, which enables computationally efficient processing and analysis for real-time analysis results and almost instant query results based on semantic language inputs. Further, the example instructions 128 are configured to render and process the graph databases 122 in graphical representations that approximate the actual underlying data structure, which are relatively easy for a user to understand compared to excess quantities of raw patient medical data or data stored in relational databases.

FIG. 2 illustrates a diagram of another embodiment of the outbreak tracking and management system 100 of FIG. 1, according to an example embodiment of the present disclosure. In the illustrated embodiment, the example outbreak management server 102 is communicatively coupled to the user device 126 via a network 202 (e.g., the Internet). The outbreak management server 102 is also communicatively coupled to data servers 204, which are configured to transmit patient data 206 for creating graph databases. The example data servers 204 are configured to generate certain data that describes a location of a patient at a particular date/time. The data servers 204 may also include data that is indicative of a patient's symptoms, physiological information, or anything else that may be relevant for determining nodes, parameters, and/or relationships for a graph database. For example, the social media server **204*a* is configured to transmit social media data 206*a* related to a patient. The social media data may include posts, tweets, images, check-in information, etc. The social media data 206*a* is processed by the outbreak management server 102 using, for example, word maps, keyword identifiers, and other textural natural language search routines to identify data for one or more nodes, relationships, and/or parameters. For example, a social media post may include information indicative that a patient checked into a certain location at a specified time/date. The example outbreak management server 102 is configured to parse the post for the location information for creating a location node. Further, the outbreak management server 102 parses the data 206*a* for the time/date for a time/date node. The outbreak management server 102 may then create relationships between a node for the patient and the location and times/date nodes, which would be stored in a graph database as: "Person (node)-STAYED (relationship)-Stay (node with start and end date/time)—IN—Location (node)". In other examples, the server 102 is configured to identify tags within the data 206** to identify contacts of a patient with other individuals at a certain location on a certain date/time.

The example outbreak management server 102 is also communicatively coupled to a demographic server **204*b*, which is configured to manage demographic information of patients and family relationships. For example, some governmental organizations maintain one or more databases of individuals, which may include the person's name, address, age, gender, race, ethnicity, etc. The databases may also include a list of other individuals that reside at the same address or are related to the person. The server 102 is configured to receive demographic data 206*b* from the server 204*b*. The server 102** analyzes the demographic data to create relationships among individuals as well as population parameter information for a patient.

The example outbreak management server 102 is further communicatively coupled to a geolocation server **204*c*, which is configured to transmit geolocation tracking data. For instance, cellular operators provide location tracking services for smartphones. The operators maintain a database that correlates a user's location (e.g., a GPS location) to a date/time the user was at the location. The server 102 receives this location data 206*c* from the geolocation server 204*c***, which it uses to create location and/or date/time nodes regarding the travels of a patient.

FIG. 3 illustrates a diagram of a further embodiment of the outbreak tracking and management system 100 of FIG. 1, according to an example embodiment of the present disclosure. In the illustrated embodiment, the outbreak management server 102 optionally receives the patient data 206 from the servers 204. In addition, the outbreak management server 102 is communicatively coupled to the HIS 104 via the network 202. In the illustrated embodiment, the server 102 may comprise a cloud-based service host that is configured to provide distributive computing across one or more locations.

FIG. 3 also shows that the user device 126 includes an application 302 (e.g., an App) that is configured to display the graph databases 122. The application 302 is also configured to enable a user of the device 126 to interact with and/or modify the graph database 122 and/or analysis data 124. The application 302 may comprise instructions that cause the device 126 to communicate with one or more APIs at the server 102 for accessing the graph databases 122 and/or the analysis data 124. The application 302 may also include instructions that specify how the graph databases 122 and/or analysis data 124 is to be rendered and displayed on the device 126. The application 302 may further include instructions that define interface tools that a user may use to modify or manipulate the graph databases 122 and/or analysis data 124. In some embodiments, the application 302 may be configured to access the patient medical data 107 at the memory device 108 via the HIS 104.

II. Outbreak Management Server Embodiment

Figure 4:
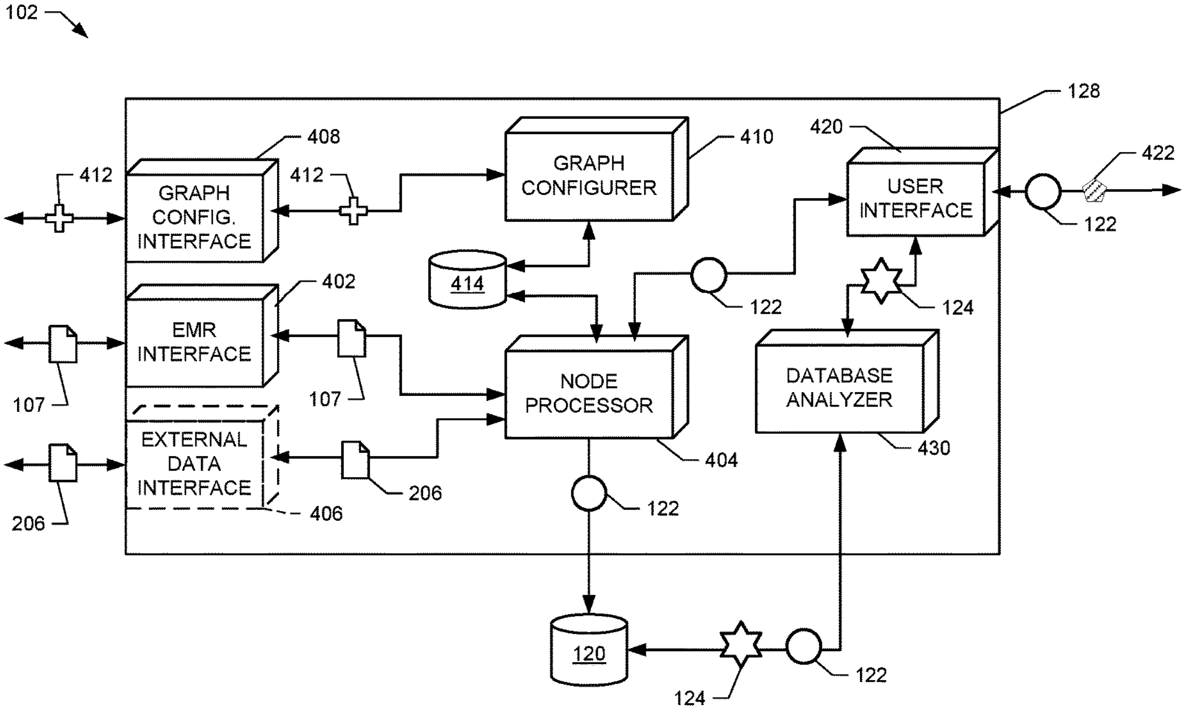
FIG. 4 shows a diagram of the outbreak management server of FIGS. 1 to 3, according to an example embodiment of the present disclosure.

FIG. 4 illustrates a diagram of the outbreak management server 102 of FIGS. 1 to 3, according to an example embodiment of the present disclosure. As disclosed above, operations of the outbreak management server 102 may be defined by the instructions 128 stored in a memory device that is communicatively coupled to the server 102. FIG. 4 shows a graphical representation of the instructions 128 as operational blocks. In some embodiments, the blocks may be combined, added, removed, or further subdivided. It should be appreciated that the graphical representation of the instructions 128 is provided to describe the operations of the server 102. Further, in some embodiments, the instructions 128 may be embodied as hardware or a combination of hardware and software, such as an Application Specific Integrated Circuit ("ASIC"), a microcontroller, and/or a processor. Additionally or alternatively, the instructions 128 may be executed by a single processor or a group of processors, such as in a distributed computing environment.

The example outbreak management server 102 of FIG. 4 includes an EMR interface 402 configured to receive or otherwise acquire a copy of the patient medical data 107 from the HIS 104. The example EMR interface 402 may include one or more instructions for accessing one or more APIs at the HIS 104 for reading the patient medical data 107 from the memory device 108. The interface 402 may additionally or alternatively be configured to transmit request messages for the patient medical data 107. In some instances, the request messages may subscribe to the patient medical data 107 such that changes to the data 107 are automatically sent from the HIS 104 to the EMR interface 402. In some embodiments, the interface 402 may periodically or continually receive the patient medical data 107 from the HIS 104 without having to send a request message.

The example interface 402 is configured to transmit received data 107 to a node processor 404. In some embodiments, the interface 402 may queue the data 107 until the node processor 404 is available. Further, in some embodiments, the interface 402 may be configured to convert the patient medical data from a first format into a second format compatible for processing by the node processor 404 or storage in a graph database. For example, the interface 402 may be configured to convert patient medical data 107 from an HL7 format to an ASCII format for storing data to an EMR or graph database. In some embodiments, the interface 402 converts the data 107 into a JSON, HTML, text, or nonSQL, format.

An external data interface 406 of the server 102 is configured to process the patient data 206 from the external third-party servers 204. Similar to the EMR interface 402, the external data interface 406 may include one or more instructions for accessing one or more APIs at the servers 204 for reading the patient data 206. The interface 406 may additionally or alternatively be configured to transmit request messages for the patient data 206. The request messages may include authentication information to access the patient data 206. The request messages may also include identifiers (e.g., a name, address, alpha-numeric code, etc.) of a patient for which information is being requested. For example, the external data interface 406 may only request information after a host node in an outbreak graph database has been created for a patient based on patient medical data 107. In some instances, the request messages may subscribe to the patient data 206 such that changes to the data are automatically sent from the servers 204 to the external data interface 406. In some embodiments, the interface 406 may periodically or continually receive the patient data 206 from the servers 204 without having to send a request message.

Again, similar to the EMR interface 402, the example interface 406 is configured to transmit received data 206 to the node processor 404. In some embodiments, the interface 406 may queue the data 206 until the node processor 404 is available. Further, in some embodiments, the interface 406 may be configured to convert the patient data from a first format into a second format compatible that is for processing by the node processor 404 or storage in a graph database. For example, the interface 402 may be configured to convert patient data 206 from a text format to an ASCII format for storing data to an EMR or graph database. In some embodiments, the interface 406 converts the data 107 into a JSON, HTML, text, or nonSQL, format.

Before the outbreak management server 102 can create graph databases, a foundation or framework for the graph databases has to be defined. The example server 102 includes a graph configuration interface 408 and a graph configurer 410 configured to enable a user to configure conditions 412 for outbreak detection and conditions for determining possible/suspected, possible, and confirmed cases. The interface 408 and the configurer 410 are also configured to enable a user specify a hierarchy of node types in a location, such as a hospital. The user-provided or system-generated information 412 is stored to a database 414 as an outbreak graph template or definition file.

It should be approached that the conditions 412 do not specify or define the structure of an outbreak graph database itself, but rather the conditions for creating different node types, determining relationships between nodes, or determining values for writing to one or more node parameters. For example, the database 414 may store a different type of graph database template for each type of disease, infection or outbreak. The Official Journal of the European Union—Commission Implementing Decision of Aug. 8, 2012 laying down case definitions for reporting communicable diseases, dated Sep. 27, 2012, which is incorporated herein by reference, defines preconditions (if appropriate), clinical criteria, and diagnostic criteria for numerous diseases or infections. In addition, the document specifies epidemiological criteria and case classification criteria (i.e., a definition of a possible/suspected case of an infection, a definition of a probable case of the infection, and/or a definition of a confirmed case of the infection) for each infection or outbreak condition. The case classification criteria are based on the clinical criteria and the diagnostic criteria. Together, this information is used for specifying parameters and determining a case classification for a case definition of diseases or infections of a host node in a graph database. In addition, the epidemiological criteria specify contraction criteria, which are used for assessing relationships between hosts to determine possibilities or susceptibility to a host or other individual's contraction of an infection.

In an example regarding Q Fever (*Coxiella burnetii*), the clinical criteria is defined as any person with at least one of the following three symptoms: fever, pneumonia, or hepatitis. Laboratory criteria are defined as at least one of: isolation of *Coxiella burnetii* from a clinical specimen, detection of *Coxiella burnetii* in nucleic acid in a clinical specimen, or a *Coxiella burnetii* specific antibody response (IgG or IgM phase II). Epidemiological criteria include at least one of exposure to a common source or animal to human transmission. While there is no 'possible' classification case definition, a 'probable' classification case definition includes any person meeting the clinical criteria with an epidemiological link and a 'confirmed' case classification includes any person meeting the clinical and laboratory criteria.

In some embodiments, the graph configuration interface 408 is configured to receive the conditions 412 from a clinician or other user (from devices 114 or 126 of FIG. 1). The graph configuration interface 408 may, for example, provide an input user interface or fields prompting a user for the case conditions. The received conditions are processed by the graph configurer 410 to define the conditions for the specified outbreak. After the conditions are defined, the example node processor 404 is configured to determine if a patient's symptoms or other medical data 107 matches the specified conditions to determine if the patient has a 'possible', 'probable', or 'confirmed' classification case for the outbreak. If so, the node processor 404 creates an episode in the outbreak graph database 122 for the patient, which may include adding a graph or node for the patient to the existing graph database of other patients/nodes with the same disease or outbreak.

In other embodiments, the graph configuration interface 408 is configured to receive the conditions 412 as source information from, for example, an electronic version of "The Official Journal of the European Union". In these embodiments, the graph configurer 410 is configured to read and parse the text to identify an infection name, preconditions, clinical criteria, diagnostic or laboratory criteria, epidemiological criteria, and case classifications. The graph configurer 410 automatically creates an outbreak template or definitions for each infection by populating the identified information into the appropriate parameters, nodes, relationships, etc. This configuration enables the interface 408 to be communicatively coupled to a health system or governmental database of infections. The interface 408 uses the connection to acquire new infection information as it is published, thereby increasing the speed at which an outbreak can be detected/tracked. It should be appreciated that outbreak conditions can also be determined for other types of outbreaks, such as food contamination or spoilage, chemical, radiation, etc.

FIGS. 6 and 7 illustrate a graphical representation 600 of the conditions 412 of FIG. 4, according to an example embodiment of the present disclosure. The example graphical representation 600 of FIG. 6 includes clinical criteria for influenza. The example graphical representation 600 of FIG. 7 includes laboratory criteria for influenza, epidemiological criteria, and case classifications for 'probable', 'possible', and 'confirmed'. The conditions 412 may be provided by a user or automatically extracted from a document or database. The example node configurer 410 is configured to create a definition file or template for an influenza outbreak graph database based on the information in the graphical representation 600. For example, the clinical criteria may be labeled as symptoms, with AND and OR logic being used to provide a computational relationship between the symptom in a definition file or template. In addition, the laboratory criteria may labeled as laboratory data types. Further, the node configurer 410 may use the epidemiological criteria to determine epidemiological links for the graph database that may correspond to higher weights for identifying potentially infected individuals. Further, the case classification includes Boolean logic of the laboratory and clinical criteria, which are used by the node configurer 410 for programming conditions for triggering 'suspected', 'probable', and 'confirmed' classifications in the graph database.

The example node processor 404 of FIG. 4 is configured to create outbreak graph databases for infections and other outbreak types that have been defined. The node processor 404 creates graph databases based on the graph database structure or framework 800 shown in FIG. 8, according to an example embodiment of the present disclosure. The example graph database structure 800 is specifically configured to record different data levels related to an outbreak. In other words, the graph database structure 800 defines relationships between different types of nodes (shown as circular elements) and the textural or sematic relationships (e.g., edges) between the nodes. The node processor 404 uses the graph database structure 800 for linking together nodes based on the specified format so as to only create meaningful links for downstream analysis. For example, the graph database structure 800 specifies that an Outbreak Node is defined by a Definition Node using a "DEFINED AS" edge or relationship. In addition, each occurrence of the outbreak is specified as an Episode Node which has a "PART OF" edge or relationship with the Outbreak Node. It should be appreciated that an unlimited number of Episode Nodes may be linked to an Outbreak Node representing hosts that are have classified cases of 'confirmed', probable', or 'possible' with respect to the disease that is associated with the outbreak. The structure 800 prevents nodes other than Episode Nodes from being linked directly with an Outbreak Node, or even Outbreak Nodes from being linked to other Outbreak Nodes.

Figure 8:
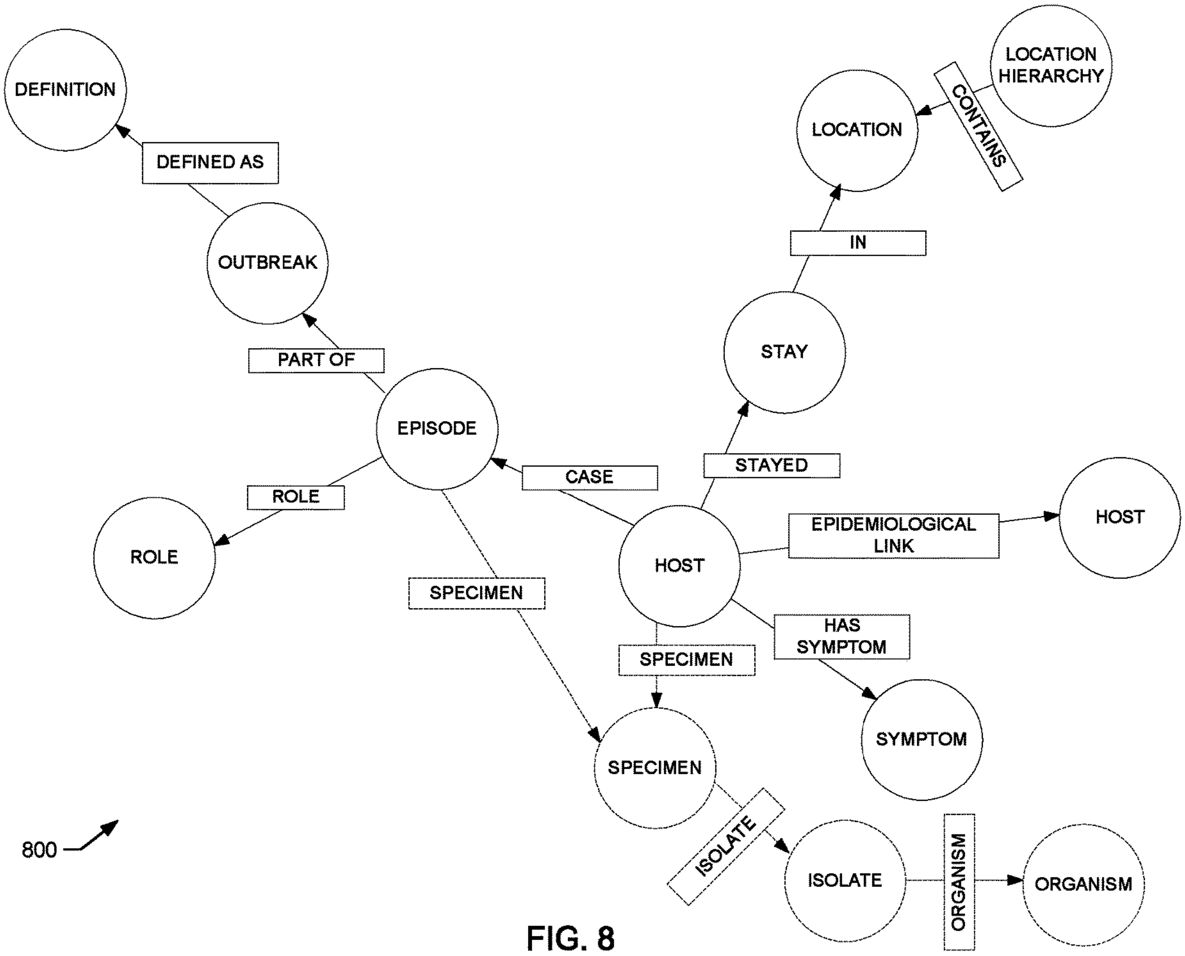
FIG. 8 shows a diagram of an outbreak graph database structure, according to an example embodiment of the present disclosure.
Figure 9:
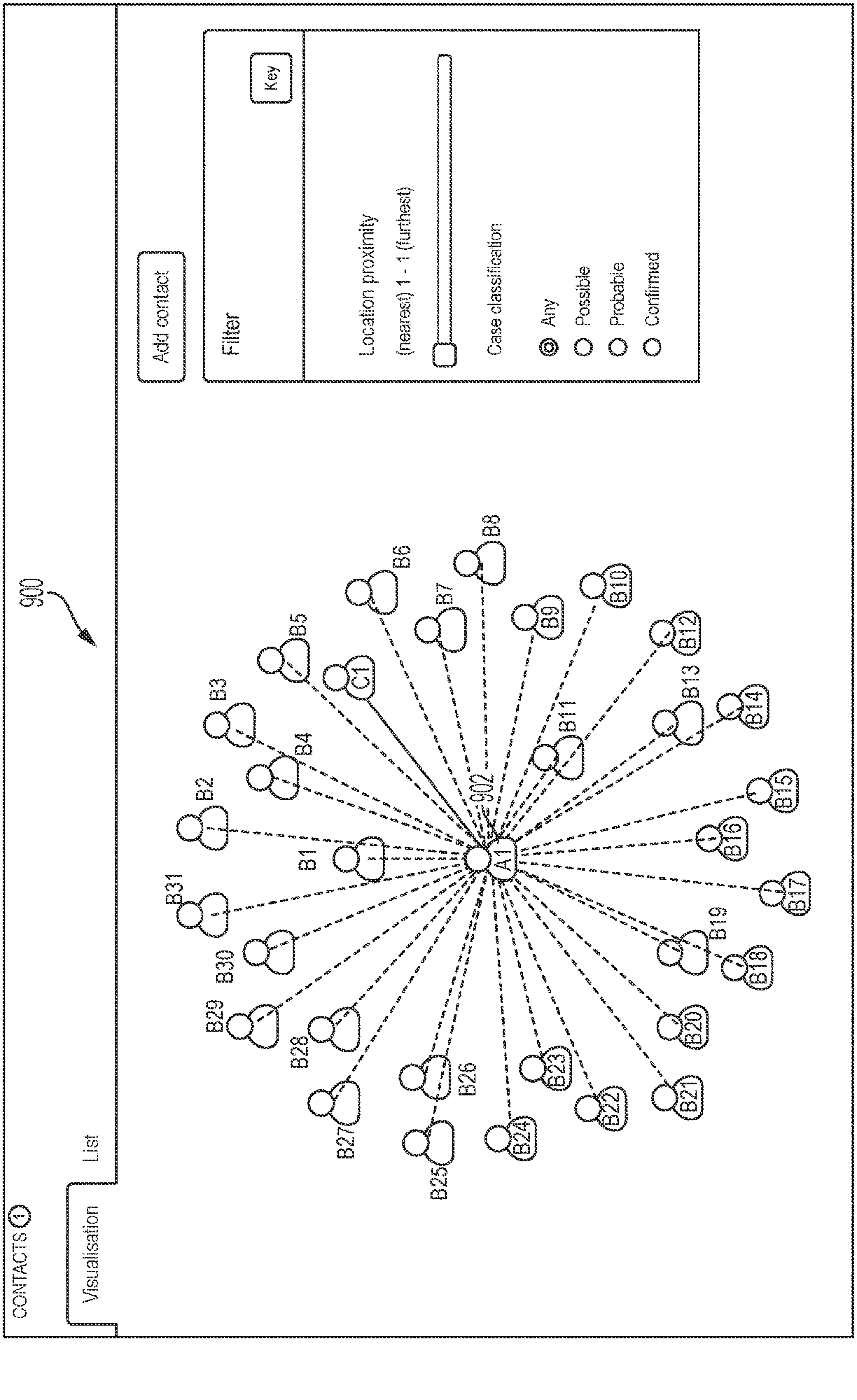
FIG. 9 shows a diagram of an interface screen of an outbreak graph database for a specified Host Node, according to an example embodiment of the present disclosure.

As illustrated in the structure 800 of FIG. 8, each Episode Node is connected to a Host Node via a "CASE" relationship or link. A Host Node may be connected to other Host Nodes via an epidemiological link, with at least some of the other Host Nodes having their own Episode Nodes linking back to the Outbreak Node (not shown). The Host Node is also connected to Symptom Nodes via a "HAS SYMPTOM" edge, relationship, or link. The Host Node may further be connected to one or more STAY Nodes via a "STAYED" relationship or link. The STAY Node is connected to a "Location Node" via an "IN" relationship or link. In some embodiments, the Location Node may be part of a larger hierarchy of Location nodes representative of a hierarchy of physical spaces in a location, as is shown in FIG. 10.

In the illustrated example, a Role Node is linked to the Episode Node via a "ROLE" edge, relationship, or link. This enables the graph database to reflect whether the same person or host acted as a carrier during an outbreak based on a certain role, such as clinician or patient. In some embodiments, an Outbreak Node may be linked to a Notes Node via a "HAS NOTE" relationship or link. The Nodes Node may specify information related to the outbreak.

The example node processor 404 is configured to generate an outbreak graph database when a patient has at least a suspected case of an infection or condition related to the outbreak. The node processor 404 may create separate outbreak graph databases for specific locations until there is sufficient data indicative of a spread of the outbreak to larger areas. For example, the node processor 404 may create different outbreak graphs for patients in different locations of a town. However, as the data provides new cases and interrelationships between patients, the node processor 404 may have sufficient information to combine the graphs together via epidemiological links to other host nodes.

The following tables provide parameters (e.g., attributes) for each of the different types of nodes shown in FIG. 8. Every Outbreak Node is connected to a Definition Node, which contains a case definition for the outbreak. As illustrated, there is a single Definition Node for each Outbreak Node. Table 1 below shows parameters of the Definition Node. Values for the parameters are identified or received from the conditions 412, shown in FIG. 4. It should be appreciated that the parameters or attributes shown in Table 1 are only illustrative and that the table may contain additional or fewer parameters or attributes. For example, some outbreaks may not have 'suspected' classification criteria.

TABLE 1

| Attribute | Description |
|---|---|
| name | Name (currently "Definition") |
| background | Background to the case (HTML) |
| time_place | Information on the time and place of the outbreak/incident (HTML) |
| clinical_criteria | Clinical criteria (HTML) |
| lab criteria | Laboratory criteria (HTML) |
| primary_mode_of_transmission | Primary mode of transmission (relationship name) |
| other_modes_of_transmission | Other modes of transmission (JSON object of multiple relationships) |
| suspected_enabled | Possible/suspected case classification applicable to this outbreak (boolean) |
| probable_enabled | Probable case classification applicable to this outbreak (boolean) |
| suspected | Criteria for determining a possible/suspected case (HTML) |
| probable | Criteria for determining a probable case (HTML) |
| confirmed | Criteria for determining a confirmed case (HTML) |
| notes | Additional notes (HTML) |
| created_at | When the node was created (populated by NeoEloquent) |
| updated_at | When the node was last updated (populated by NeoEloquent) |

For any given outbreak, there exists Hosts (e.g., infection sources) who have cases in Outbreaks. The cases are labeled as Episode Nodes. The following cypher query for the graph database illustrates an example host linkage to an outbreak:

| People who have cases in an outbreak |
|---|
| MATCH (p:Host) - [:CASE] –> (e:Episode) - [:PART_OF] –> (o:Outbreak) RETURN p, e, o |

The cypher query may be filtered for non-null case classifications so as to focus on individuals who are 'affected' by the outbreak. When people (e.g., hosts) are added to an outbreak, the server 102 is configured to create the same relationship (i.e. with a connecting Episode Node), but a case classification may not be initially set. This is so that there is a short-list of people or hosts for investigation before ultimately assigning case status. This process is followed whenever a host is added to an outbreak or when individual hosts are synchronized from a connected server 204. Table 2 below shows parameters of an Episode Node. The node processor 404 determines the parameter values for the Episode Node from, for example, a patient's medical data 107. The start_date/start_ts of the Episode Node is used to determine the 'incidence' (e.g. an outbreak epicurve) to indicate when the host or individual became part of the outbreak. The classification may change at any time as a host may transition in between 'possible', 'probable' & 'confirmed' case classifications. The node processor 404 uses the Definition Node to determine the case classification for the Episode Node. For example, symptoms and laboratory data 107 of the patient are matched by the node processor 404 to the case classification conditions in the Definition Node to determine if the patient is suspected, possible, or confirmed for a disease associated with the outbreak. In other examples, a clinician may provide or enter the classification. In these other examples, the node processor 404 may determine a recommended classification, which is displayed to a clinician to confirm after reviewing the patient's information in relation to the classification conditions.

TABLE 2

| Attribute | Description |
|---|---|
| start_date | Human readable Y-m-d H:i:s date of the start of the case |
| start_ts | Timestamp version of the above (better for querying) |
| classification | NULL or '?' (possible), 'P' (probable), 'C' (confirmed) |
| immunization_status | Immunization status at case onset (json terminology source) |
| immunization_type | Type of immunization (json terminology source) |
| acquisition_of_infection | e.g. hospital-acquired (json terminology source) |
| death certificate | If person died was the outbreak/incident organism/related condition recorded on the death certificate? |
| created_at | Automatically set by NeoEloquent |
| updated_at | Automatically set by NeoEloquent |

In any single outbreak, a single Episode Node may be identified as the index case. This is identified by a one-to-one relationship in between the Outbreak Node and the Episode Node called INDEX.

The example Host Node includes parameters that provide information related to the host. This includes a parameter providing an indication or flag as to whether the host is a person, animal, fomite, object, etc. The Host Node may also include parameters regarding a name, demographics, physical attributes, medical data 107, or other information related to a person. The node processor 404 may analyze or parse the data 107 and 206 for information to populate the parameters. In some examples, the node processor 404 may use word maps, natural language matches, label/field identifiers, and/or metadata to determine a property for population.

The Role Node shown in FIG. 8 may be linked to the Episode Node and provide a role for at least each some Outbreak Nodes that are linked to people. Table 3 below shows examples of roles, which include a patient, staff, and public. It should be appreciated that an Episode Node may have more than one Role Node, where for example, staff of a hospital may eventually also be a patient.

TABLE 3

| Role 'role' | Attribute | Description |
|---|---|---|
| Staff | stopped_work | Date staff member stopped work |
| Staff | returned_to_work | Date staff member returned to work |
| Patient | discharge_delayed | Whether or not discharge/ transfer was delayed as a result of the outbreak/ incident (Y/N) |
| Patient | surgery_cancelled | Where or not surgery was cancelled as a result of the outbreak/incident (YIN) |

The example Symptom Node is linked to a Host by the node generator 404 of the server 102 using, for example, the following cypher query:

| Cypher query to see people and symptoms |
|---|
| MATCH (p: Person) - [:HAS_SYMPTOM] –> (s: Symptom) RETURN p, s |

The node generator 404 may determine symptoms from the patient's medical data 107 by, for example, searching for symptom keywords. Table 4 below shows example parameters or attributes of the Symptom Node that may be determined by the node generator 404. The example node generator 404 uses the symptom parameters to determine a case classification of a host for the Episode Node using the defined criteria. As new symptoms are received, the host generator 404 adds the new symptoms as new Symptom Nodes that are connected to the Host Node, and updates a case classification accordingly. In addition, if a symptom ends, the host generator 404 notes the ending of the symptom. In some embodiments, the node generator 404, via user interface 420, receives an input message 422 from device 114 or 126. The input message 422 includes symptom information provided by a clinician. The message 422 may also include a case classification. In some embodiments, the user interface 420 may display an input window for a selected patient that enables a user to select a symptom from a drop-down list and/or select an icon representative of the case classification.

TABLE 4

| Attribute | Details |
|---|---|
| uuid | Unique identifier |
| symptom | Symptom-see constants in App\Symptom |
| start_date | start date of symptom (ATOM format) |
| end_date | end date of symptom (ATOM format) |
| created_at | Automatically set by NeoEloquent |
| updated_at | Automatically set by NeoEloquent |

The example graph database structure 800 of FIG. 8 illustrates that Host Nodes are linked together via epidemiological links. Table 5 below shows examples of types of epidemiological links. In some examples, Table 5 may include a risk score or weight based on the link that corresponds to how a disease is typically transmitted. Links that are not associated with transmission may be assigned a lower risk score when a database analyzer 430 of the server 102 searches for potential infected hosts. In other instances, Table 5 may contain only epidemiological links that are relevant towards transmission.

TABLE 5

| Attribute | Description |
|---|---|
| AIRBORNE | Airborne |
| ANIMAL_RESERVOIRS | Animal reservoirs |
| ANIMAL_TO_PERSON_CONTACT | Animal to person contact |
| CONTAMINATED_OBJECTS | Contaminated objects |
| DROPLET_SPREAD | Droplet spread |
| ENVIRONMENTAL_RESERVOIRS | Environmental reservoirs |
| FOOD_AND_DRINKING_WATER | Food and drinking water |
| INSECT_BITES | Insect bites |
| PERSON_TO_PERSON_CONTACT | Person-to-person contact |

In some embodiments, the node generator 404 is configured to determine epidemiological links (or potential links for confirmation) between hosts using data 107 and/or 206. For example, social media or demographic relationship data may be used to determine epidemiological links. In other examples, geographic location may be used to determine when two hosts were in the same location at the same time. In other examples, a clinician's notes may include a list of individuals that came in contact with a patient. In yet other examples, a treatment schedule of a patient, included within the data 107, may identify which clinicians came in contact with a patient. The node generator 404 is configured to use word maps, fields, labels, or metadata to identify names from the data 107 and/or 206 for identifying hosts and potential epidemiological links between the hosts.

In some embodiments, the user interface 420 of FIG. 4 may display an interface screen 900 that provides a graphical representation of links or potential links between hosts, for a given selected host 902. Upon request, the database analyzer 430 analyzes links (or links labeled as 'potential links') between a selected host and other hosts to determine and render the graphical representation. A clinician interacts with the interface screen 900 by selecting potential links and assigning a corresponding epidemiological link. Selection of the epidemiological link by the clinician causes the node generator 404 to update a link between selected hosts in the graph database with the received epidemiological link. For example, a potential link is changed by the node generator 404 to an epidemiological link.

Returning to FIG. 8, the Host Node is linked to a Location Node via a Stay Node. The Stay Node specifies start and end dates and/or times in which a host was at a particular location. Table 6 below shows example parameters or attributes of the Stay Node. The example node generator 404 determines the date/time, for example, from the patient medical data 107 corresponding to patient admittance and tracking within a medical facility. For example, a patient record may indicate that a patient was located in Bed A of Room 1774 of an Acute Care Ward or care area for a week in April 2018. The node generator 404 uses metadata, data labels, fields, etc. to locate the date, which it uses to populate as a value into the appropriate parameters or attributes of the Stay Node. In other examples, a user may provide the dates/times via the user interface 420. Further, the node generator 402 may use geolocation data 206 to determine date/time information. The example date/time information may be used by the data analyzer 430 to determine which hosts were in the same location at the same time.

TABLE 6

| Attribute | Description |
|---|---|
| start_date | Human readable start date of the stay |
| start_ts | Timestamp start date of the stay |
| end_date | (Optional) human readable end date of the stay |
| end_ts | (Optional) timestamp end date of the stay |
| readonly | Node may not be edited in the UI (for stays imported from a third-party system) |
| created_at | When the node was created-Recorded automatically by NeoEloquent |
| updated_at | When the node was last updated-Recorded automatically by NeoEloquent |

The Location Node includes parameters that identify a location. Table 7 below shows an example of parameters for a Location Node. In addition, a location node may include parameters for GPS coordinates, a street address, a building name, and/or a place of interest. The node generator 404 uses the data 107 and/or 206 to determine values for the parameters or attributes similar to determining a date/time for the Location Node.

TABLE 7

| Attribute | Description |
|---|---|
| uuid | Unique identifier of a location |
| name | Name of the location |
| type | Type of the location: e.g., room, bay, hospital group, etc. |
| risk | Location proximity risk score (see above) |
| readonly | Set to true if the location data is imported from a third party system (see below') |
| created_at | When the node was created-Recorded automatically by NeoEloquent |
| updated_at | When the node was last updated-Recorded automatically by NeoEloquent |

Figure 10A:
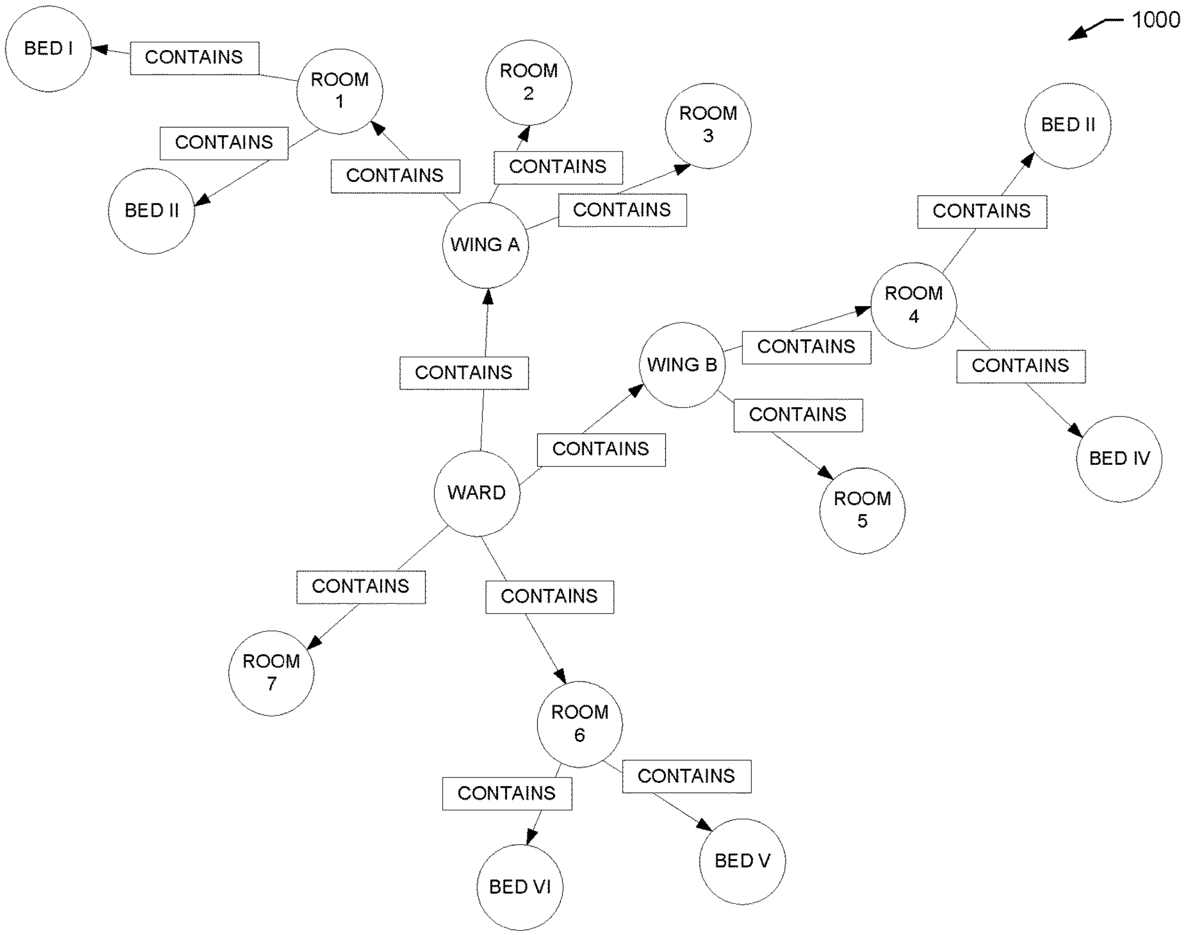
FIG. 10A shows a diagram of a hierarchical location map for use with a graph database, according to an example embodiment of the present disclosure.

In many embodiments, a location is part of a larger hierarchical location. In these embodiments, the link to the Stay Node corresponds to a Location Node lowest in the hierarchy. The hierarchy may correspond to an organization in a geographic location or physical space, such as a hospital. The example graph configurer 410 of FIG. 4 is configured to automatically create a hierarchical location map 1000, as shown in FIG. 10A from imported data, which may specify a hierarchical structure of a location. In other examples, the graph configurer 410 enables a user to create the hierarchical location map 1000. As shown in FIG. 10A, each sub-location is linked to a higher-order location via a "CONTAINS" relationship or link. In the illustrated example, a hospital Ward Location Node contains Wing Location Nodes A and B, which each contains a number of Room Location Nodes. In addition, some Room Location Nodes directly connected to the Ward Location Node without connection to a Wing Node. Further, some Room Location Nodes connect to separate Bed Location Nodes. While the map 1000 in FIG. 10A corresponds to a hospital, in other examples, the graph configurer 410 may create relational maps for businesses, neighborhoods, cities, commercial/residential buildings, public spaces, transportation systems, etc. The Location Nodes are used by the database analyzer 430 to determine a relational and/or physical distance between hosts during designated times/dates.

In some embodiments, the Location Nodes may include a risk score, which provides a numerical indication of a risk of infection of hosts corresponding to a distance between locations. The example database analyzer 430 may use the risk scores for locations to identify potential hosts that have epidemiological links to other hosts. For example, patients in adjacent beds may be assigned relatively high risk scores for their respective Bed Nodes. Table 8 below shows an example of risk scores for different Location Nodes.

TABLE 8

| Node Type | Description | Risk Score |
|---|---|---|
| Location: Bed | A space that is allocated for sleeping/laying on. This is not the physical bed/trolley that may be moved about, but the space it may occupy | 1 |
| Location: Room | A space that is allocated as a room | 2 |
| Location: Corridor | Any corridor within a Building that may connect room | 3 |
| Location: Ward | A Ward is a section of a medical facility that may contain rooms and other types of location | 4 |
| Location: Level | A Level in a multi-level Building/Structure | 5 |
| Location: Wing | A Wing within a Building, this often contains levels, rooms and corridors | 6 |
| Location: Structure | Any non-residential building or structure. This may contain rooms, corridors, wings, etc. It may not have walls or a roof, but is considered a defined/allocated space | 7 |
| Location: Building | A dwelling including private houses, flats, hospitals, and hotels. Usually used to reference a location where a person/patient may reside | 8 |
| Location: Street | A defined path to travel between 2 points that has a known name | 9 |
| Location: Site | A collection of buildings or other locations such as a site or a campus | 10 |
| Location: Hospital | A medical facility specific collection of buildings | 10 |
| Location: Area | A zone, region, postcode, zip code | 11 |
| Location: HospitalGroup | A group of hospitals such as a Health Board/Authority | 11 |
| Location: County | A county, province, or state | 12 |
| Location: Country | A nation with its own government | 13 |

In some embodiments, the Ward Location (or other centralized Location Node) includes parameters or attributes that provide general (e.g., survey) information relevant for the location. The parameters may be related to the outbreak and/or related to an activity level of the location. In some embodiments, the survey information may be its own node (e.g., a Survey Node), which is linked to the Location. Table 9 shows an example of parameters or attributes of a Survey or Location Node regarding activity level. The user interface 420 enables a user to provide the information in Table 9. Additionally or alternatively, the node generator 404 is configured to read hospital patient tracking information to determine an overall activity for a particular location. For example, the node generator 404 may determine a number of patients in beds for a care area compared to a total number of beds. The database analyzer 430 may display the information in Table 9 to show how activity level of a location changes or corresponds to an outbreak.

TABLE 9

| Attribute | Description |
|---|---|
| date | Human readable date (Y-m-d) |
| date_ts | Timestamp of the date of the survey (at 00:00 hours) |
| specialty | Specialty of the ward (text) |
| closed | Boolean: whether or not the ward is closed |
| rooms | Number of bays/rooms |
| rooms_closed | Number of bays/rooms closed |
| cohorted | Number of cohorted patients |
| empty_beds | Number of empty beds (at 10 am) |
| isolation_rooms | Number of isolation rooms |
| staffed_beds | Number of staffed beds |
| created_at | When the node was created-recorded automatically by NeoEloquent |
| updated_at | When the node was last updated-recorded automatically by NeoEloquent |

In some embodiments, the example node processor 404 receives batch information regarding patients in a hospital during a time period related to an outbreak. In these embodiments, the node processor 404 may create clusters of nodes that are linked together by the hospital Location Nodes. As more property values are identified from received patient medical data 107, the node processor 404 determines relationships (e.g., epidemiological links) between the patients. Table 10 below shows nodes and relationships of a graph database that the node processor 404 may use to synchronize different clusters of one or more patients among the same location. The database analyzer 430 determines, for example, from the data in Table 10 that an outbreak is local to a particular hospital ward or care area or room level.

TABLE 10

| Node | Details |
|---|---|
| Host: Person | Each patient will have a unique Host Person node |
| Stay | Each period of ward/room/bed occupancy will be represented by a Stay node |
| Location: HospitalGroup | A hospital group location |
| Location: Hospital | A hospital location |
| Location: Ward | A ward location |
| Location: Room | A room level location |
| Location: Bed | A bed level location |

In some instances, the node processor 404 is configured to create a single graph database for an outbreak type per location. As new patients are admitted or include symptoms, the example node processor 404 is configured to add the patients as Host Nodes to the graph database. Tracking patients that do not show symptoms, but are in the same location as an outbreak, enables the database analyzer 430 to identify patients that are vulnerable to an outbreak.

In some embodiments, the node processor 404 is configured to include microbiology information within a graph database. As illustrated in FIG. 8, each Host Node may be connected to a Specimen Node via a “SPECIMEN” edge, relationship, or link. Additionally, the corresponding Episode Node of the Host Node may also have a “SPECIMEN” edge or relationship with the Specimen Node. This linking accounts for a Host potentially having many different microbiology specimens, which may or may not be relevant to an outbreak. Table 11 shows example parameters or attributes of the Specimen Node.

TABLE 11

| Attribute | Description |
|---|---|
| uuid | string “{lab_request_id}#{specimen_number}# |
| lab_request_id | The laboratory request ID |
| specimen_number | The specimen number |
| readonly | (boolean) indication that this is imported data so is read only in the UI |
| status | The PFA status of the specimen result (Preliminary, Final or Amended) |
| taken | Human readable date/time of when the specimen was taken (Y-m-d H:i:s) |
| taken_ts | Timestamp when the specimen was taken |
| lab | Laboratory where the specimen was taken |
| type | Specimen type |
| created_at | When the node was created |
| updated_at | When the node was last updated |

Each Specimen Node may be linked to an Isolate Node via an “ISOLATE” edge or relationship. The Isolate Node specifies an isolate within specimen results. Table 12 below shows example parameters for the Isolate Node.

TABLE 12

| Attribute | Description |
|---|---|
| uuid | String “{lab_request_id}#{specimen_number}#{organism_code}” |
| readonly | (boolean) indication that this is imported data so is read only in the UI |
| result_status | PFA result status of the isolate (Preliminary, Final, or Amended) |
| created_at | When the node was created |
| updated_at | When the node was last updated |

An Isolate Node may be connected to an Organism Node via an "ORGANISM" edge or relationship. The Organism Node identifies a single organism found in an isolation routine. Table 13 below shows example parameters of the Organism Node.

TABLE 13

| Attribute | Description |
|---|---|
| uuid | Code for the organism (the organism code from ICNet) |
| readonly | (boolean) indication that this is imported data so is read only in the UI |
| name | Name of the organism |
| created_at | When the node was created |
| updated_at | When the node was last updated |

Figure 10B:
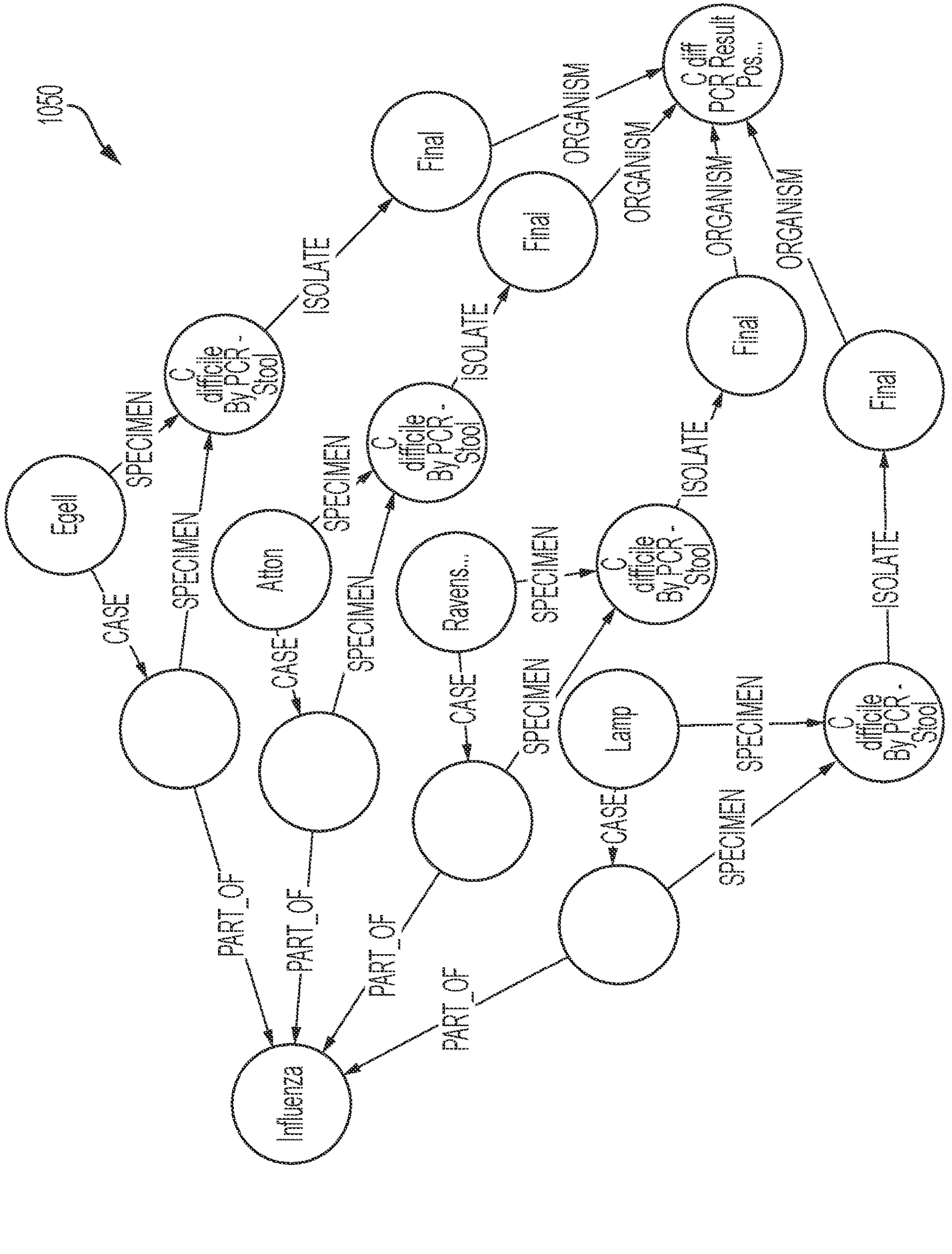
FIG. 10B shows a diagram of a graph database that includes Specimen Nodes, Isolate Nodes, and Organism Nodes, according to an example embodiment of the present disclosure.

In some examples, the node generator 404 may be configured to use the Preliminary, Final, Amended, and Deleted ("PFA(D)") system for the specimen result and isolate level. FIG. 10B illustrates a graph database 1050 that includes Specimen Nodes, Isolate Nodes, and Organism Nodes, according to an example embodiment of the present disclosure. The graph database 1050 shows that specimens and isolates from different hosts are traced back to the same organism. Such information is useful by not only showing a spread of an outbreak, but also a biologic that is responsible (or suspected) for the outbreak.

In some examples, the graph database may replace the specimen, isolate, and organism with similar nodes for identifying exposure to chemical substances, radiation types, etc.

Figure 11:
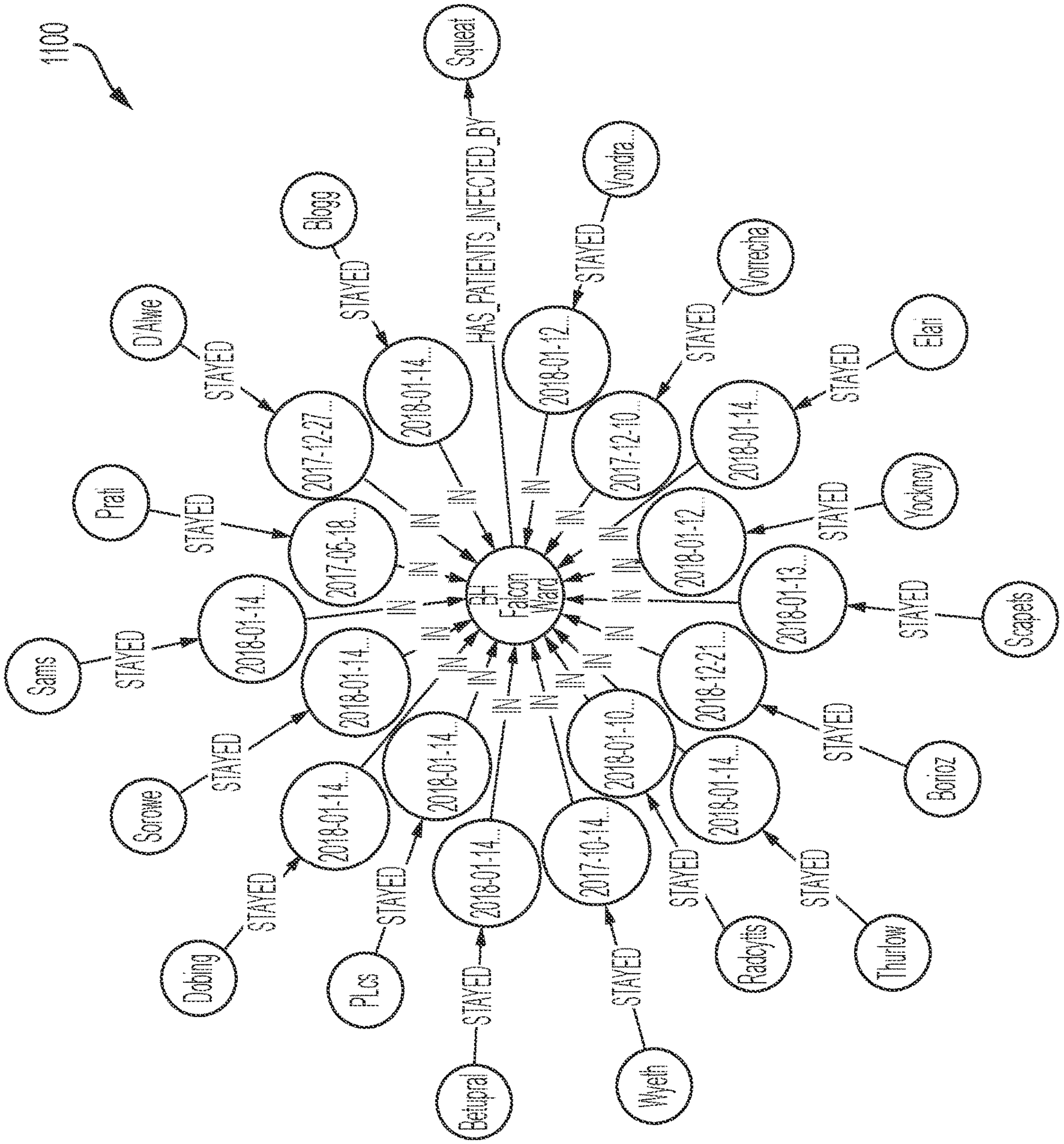
FIG. 11 shows a diagram of an example graph database for a Ward Location Node, according to an example embodiment of the present disclosure.

FIG. 11 illustrates an example graph database 1100 for a Ward Location Node, according to an example embodiment of the present disclosure. The graph database 1100 may be rendered by the database analyzer 430 in response to view relationships relative to the Ward Location Node. In this example, the database analyzer 430 may compress or hide the location hierarchy to view Stay and Host Nodes that have a relationship with the Ward Location Node. In some instances, the database analyzer 430 is configured to color code the Host Nodes based on their case classification to an outbreak to visually indicate the spread of an outbreak relative to the Ward Location Node.

Figure 12:
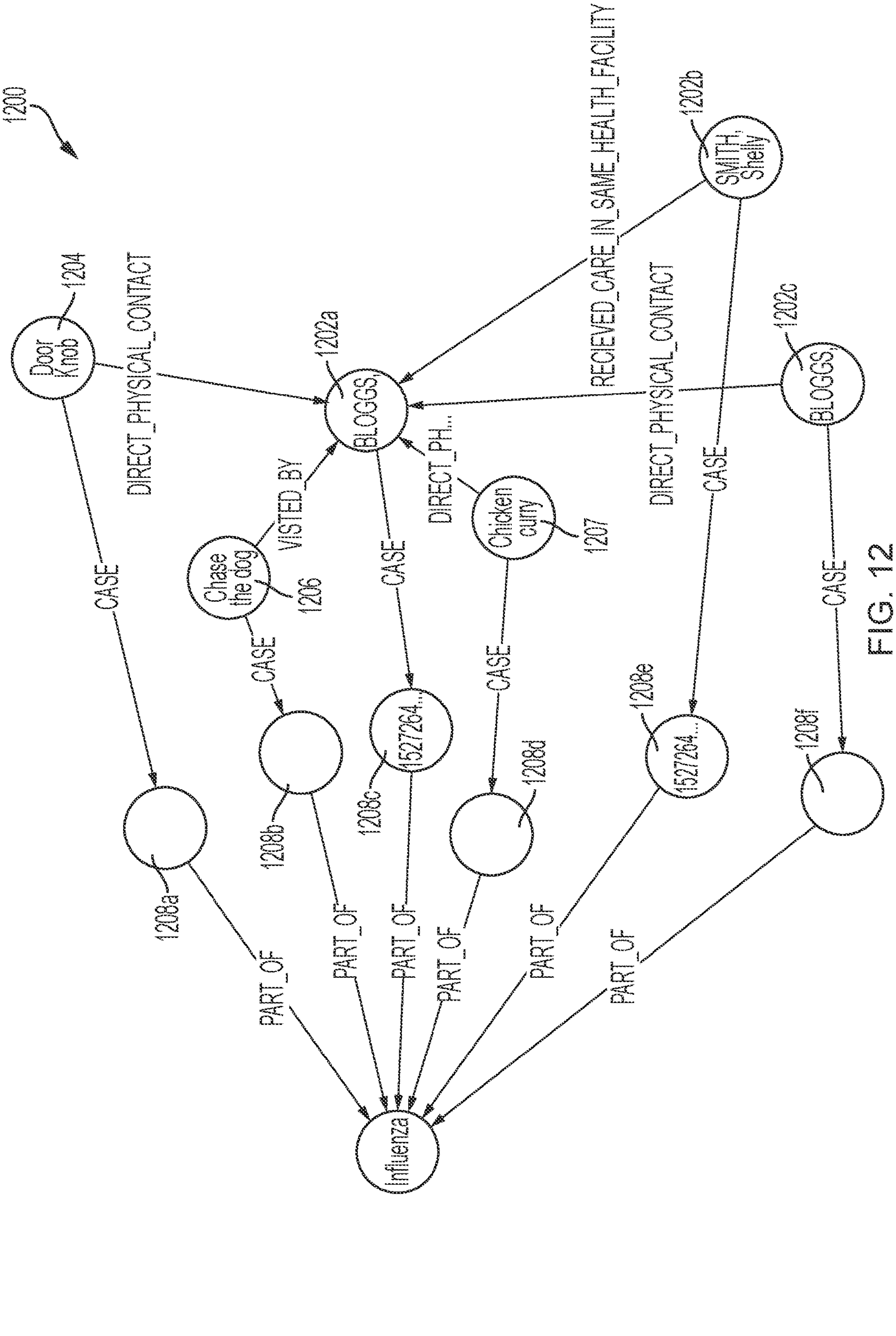
FIG. 12 shows a diagram of an example graph database for an Influenza Outbreak Node, according to an example embodiment of the present disclosure.

FIG. 12 illustrates an example graph database 1200 for an Influenza Outbreak Node, according to an example embodiment of the present disclosure. In this example, different types of host nodes are shown, with Host Nodes 1202 corresponding to persons and Host Nodes 1204, 1206, and 1207 corresponding to fomites or objects. The example node generator 404 is configured to generate a separate Episode Node 1208 for each of the Host Nodes. However, only the Episode Nodes 1208*c* and 1208*e* that are linked to a confirmed or probably case of influenza in a person are provided a case number. In contrast, the other Episode Nodes 1208*a*, 1208*b*, 1208*d*, and 1208*f* are not linked to a confirmed or probably case of influenza and accordingly are not assigned a case number. In addition, the example node generator 404 provides epidemiological links between the Host Nodes 1202, 1204, 1206, and 1208. In some instances, the node generator 404 determines the links from data 107 and 206. In other instances, the links are specified by a clinician via the user interface 420.

In some embodiments, different types of outbreaks may be part of the same graph database. In other words, each outbreak may be a separate cluster, with clusters linked together based on location and/or hosts. For example, for a particular, location, some hosts may be linked to a first outbreak while other hosts are linked to a second outbreak. The interrelation between outbreaks enables the database analyzer 430 to determine and display information regarding vulnerability of patients to certain overlapping outbreaks or determine correlation between different outbreaks. The database analyzer 430 is configured to filter a graph database for a single outbreak type by removing or hiding nodes that are related to other outbreaks.

Figure 13:
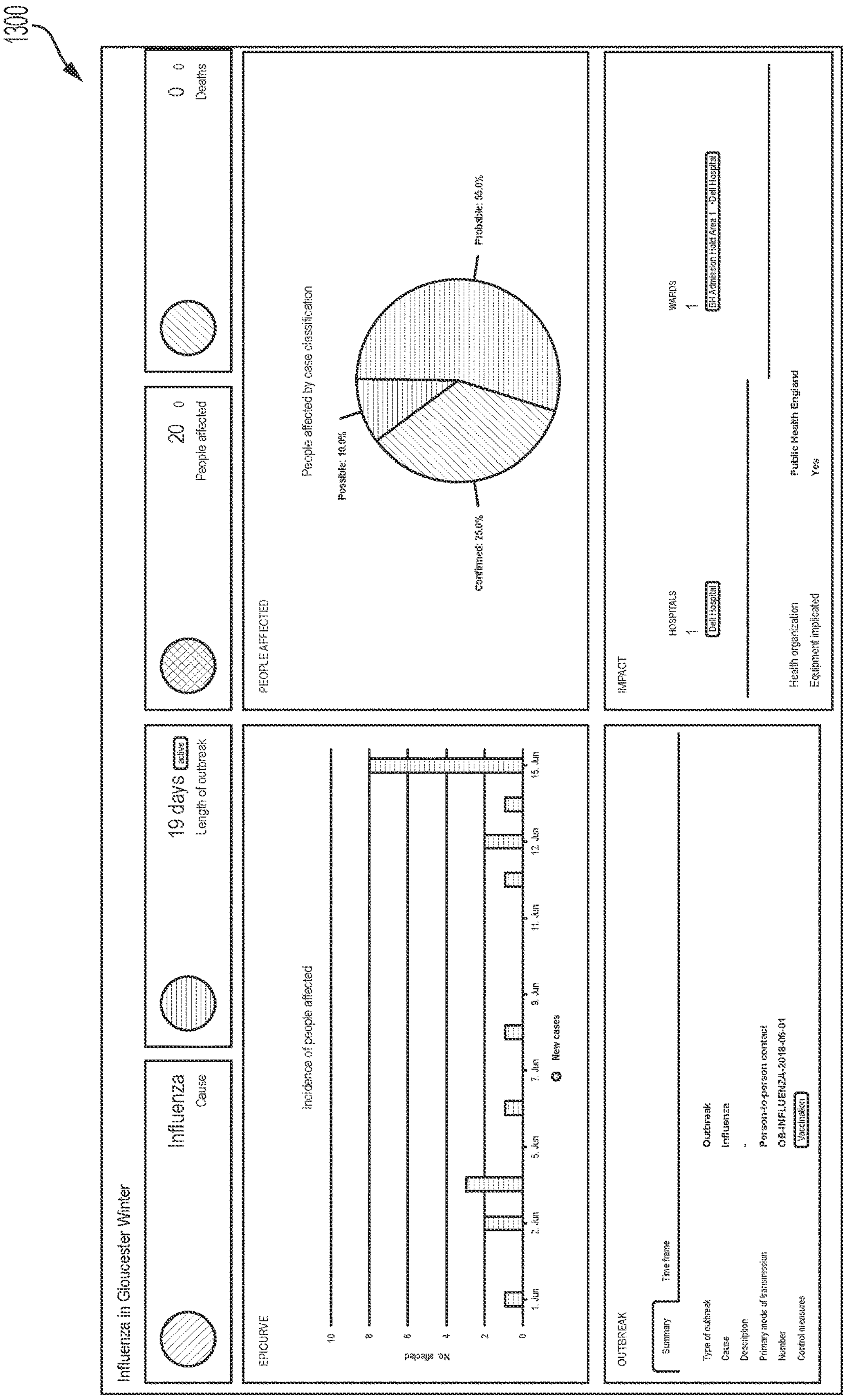
FIGS. 13 to 18 show diagrams of example interface screens of outbreak analysis data determined from an outbreak graph database, according to an example embodiment of the present disclosure.

FIG. 13 shows a dashboard interface 1300 that is configured to be rendered by the database analyzer 430, according to an example embodiment of the present disclosure. The dashboard interface 1300 includes separate sections that provide an overview for a selected outbreak. The database analyzer 430 analyzes, for example, nodes related to the specified outbreak (e.g., influenza) to determine, for example, a length of the outbreak, a total number of people affected, a total number of deaths attributable to the outbreak, a timeline of incidence, and a graph of case classification.

Figure 14:
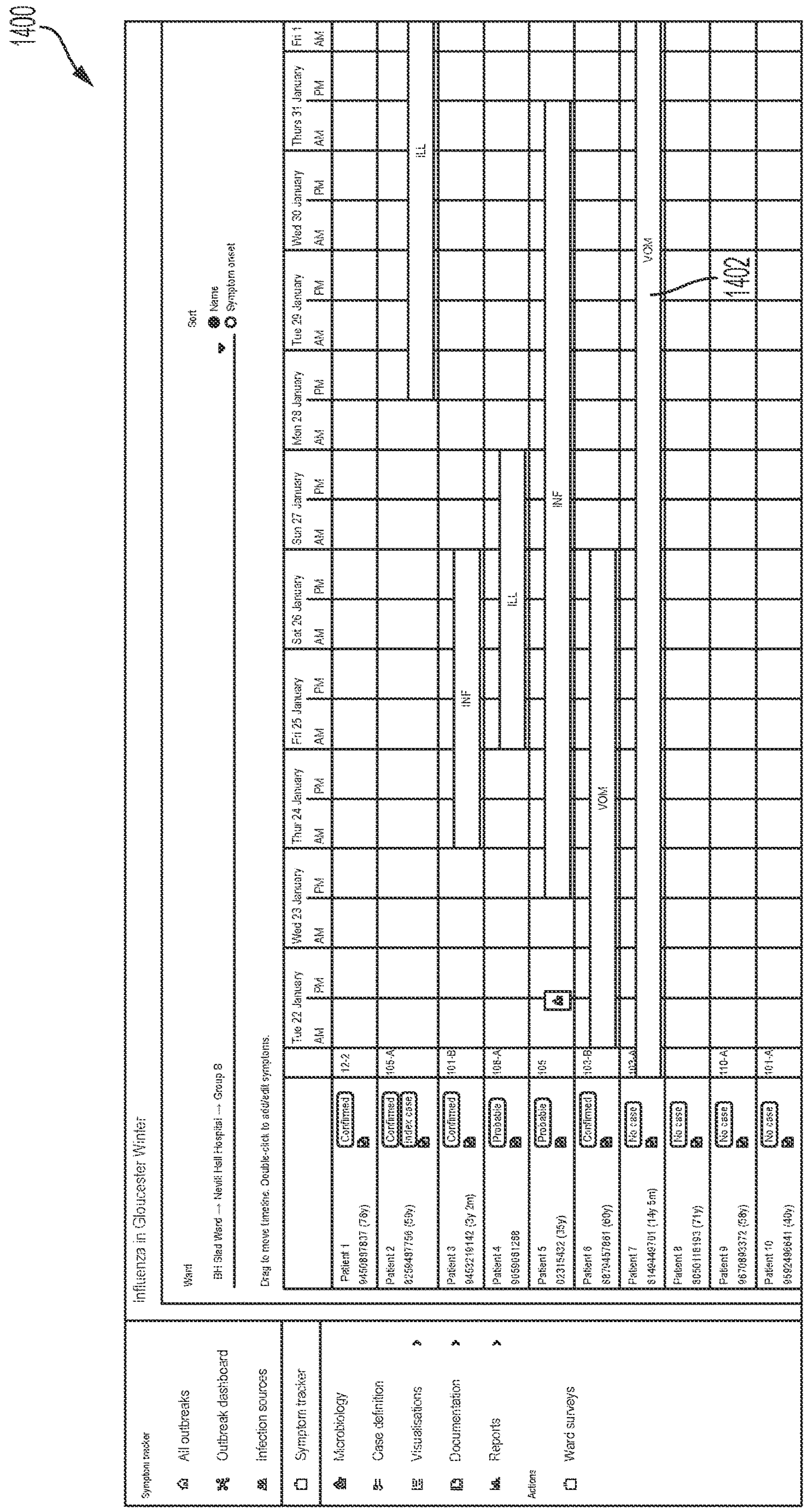

FIG. 14 shows a symptom tracker interface 1400 that is configured to be rendered by the database analyzer 430, according to an example embodiment of the present disclosure. The database analyzer 430 is configured to determine, using Host and Symptom Nodes, which patients had a particular symptom and the corresponding time period for the symptom. The interface 1400 also includes, under a patient name, a location of the patient or identifier and demographic information. Such information provides an indication of all patients showing at least one symptom that may be related to an outbreak. In some embodiments, the interface 1400 is interactive. For example, the interface 1400 may include a filter feature to filter by location, case classification, etc. In response to a request for filtering, the database analyzer 430 determines the appropriate information to display from the outbreak graph database. In other embodiments, the interface 1400 is configured to enable a clinician to move, expand, or shorten a time period for a symptom, such as symptom 1402 for 'vomiting'. The interface 1400 transmits commends provided by the clinician to the node processor 404, which adjusts the parameters in the Symptom Node accordingly (e.g., changes the duration of the symptom).

Figure 15:
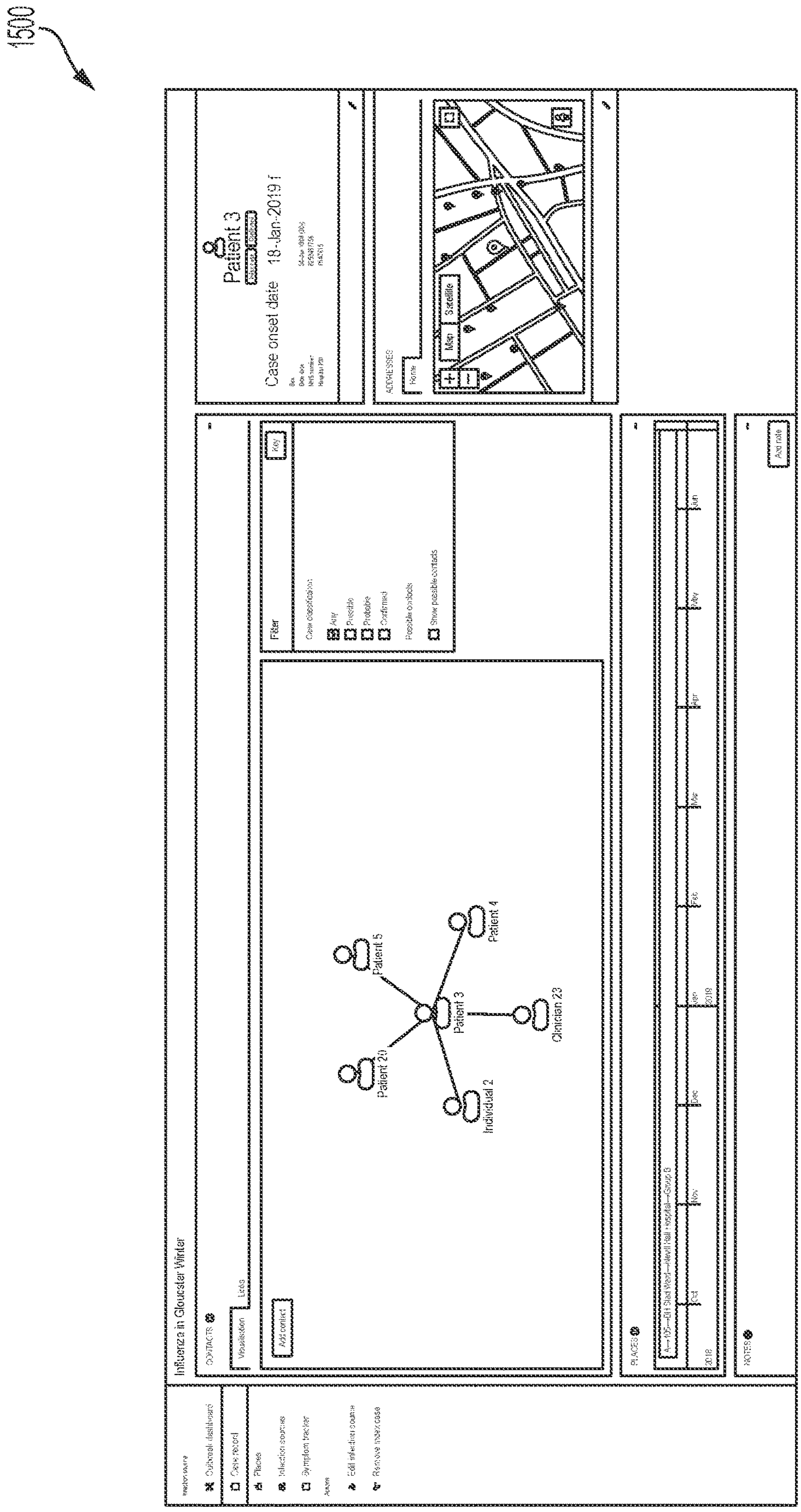

FIG. 15 illustrates a diagram of a patient interface screen 1500 for a patient (i.e., Patient 3) associated with a Host Node of an outbreak, according to an example embodiment of the present disclosure. The database analyzer 430 determines information to display in the interface screen 1500 based on patient information, relationship with other Hosts and Time/Date-Location information. A clinician may view the screen 1500 by selecting a patient in the screens/interfaces 1200 and 1400 or by providing a query entry of a patient's name or identifier. The interface 1500 may provide an overview of a patient's locations over time, including a map of those locations. The interface screen 1500 may also display a graphical relationship between the patient and other Hosts that the patient came into contact with at certain identified locations. The interface screen 1500 further shows which of those other Host Nodes have a confirmed or probable case of influenza, for example.

Figure 16:
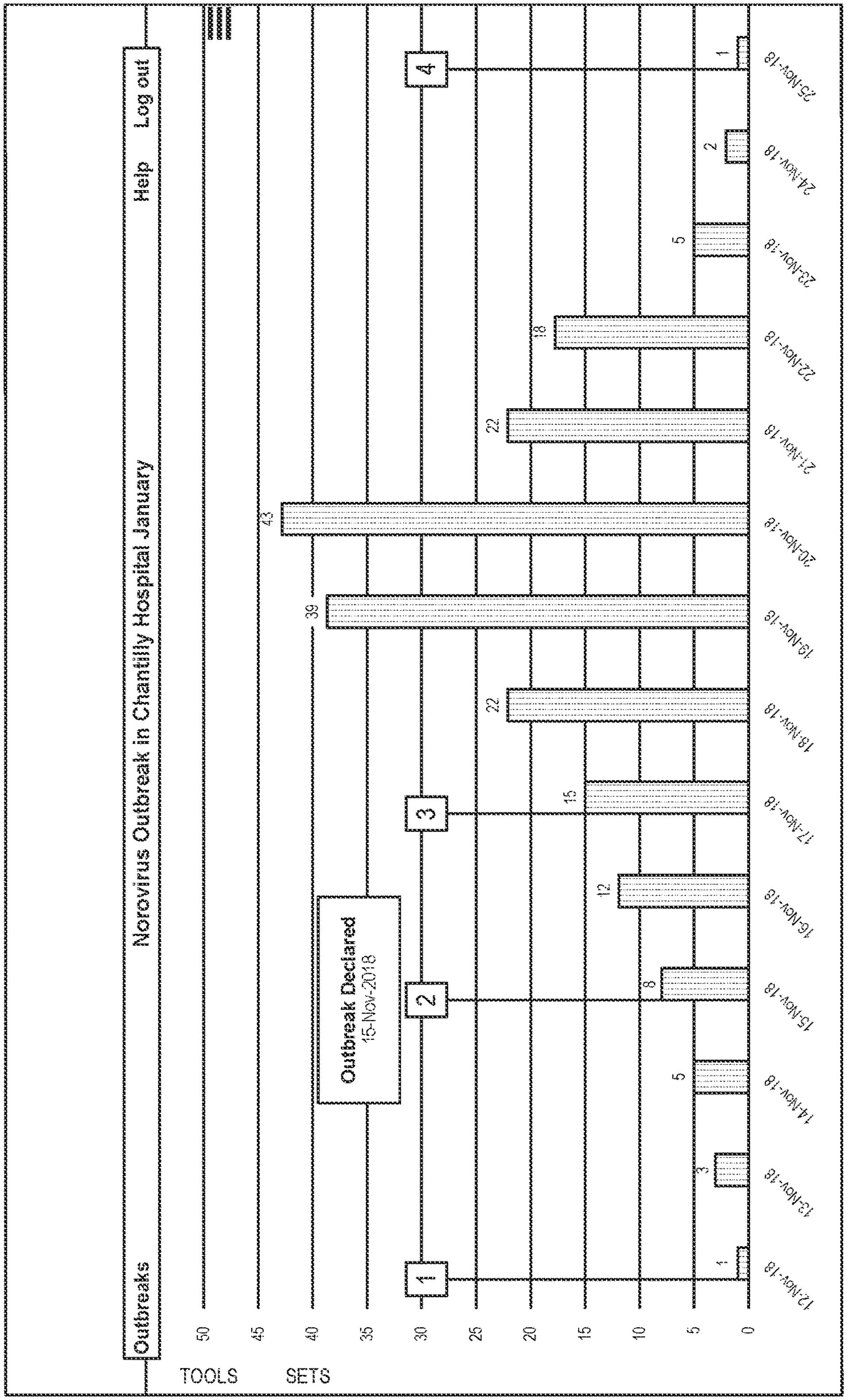

FIG. 16 illustrates a diagram of an outbreak interface screen 1600 for a Norovirus Outbreak, determined by the database analyzer 430, according to an example embodiment of the present disclosure. In the illustrated example, the database analyzer 430 receives a request to view dates of occurrence of the Norovirus at a specified location. In response, the database analyzer 430 analyzes a graph database for nodes related to Norovirus and compiles the information from case classifications of Hosts corresponding to patients/persons. In some examples, the interface screen 1600 may include options for selection that cause the database analyzer 430 to display confirmed cases compared to suspected and probable cases.

Figure 17:
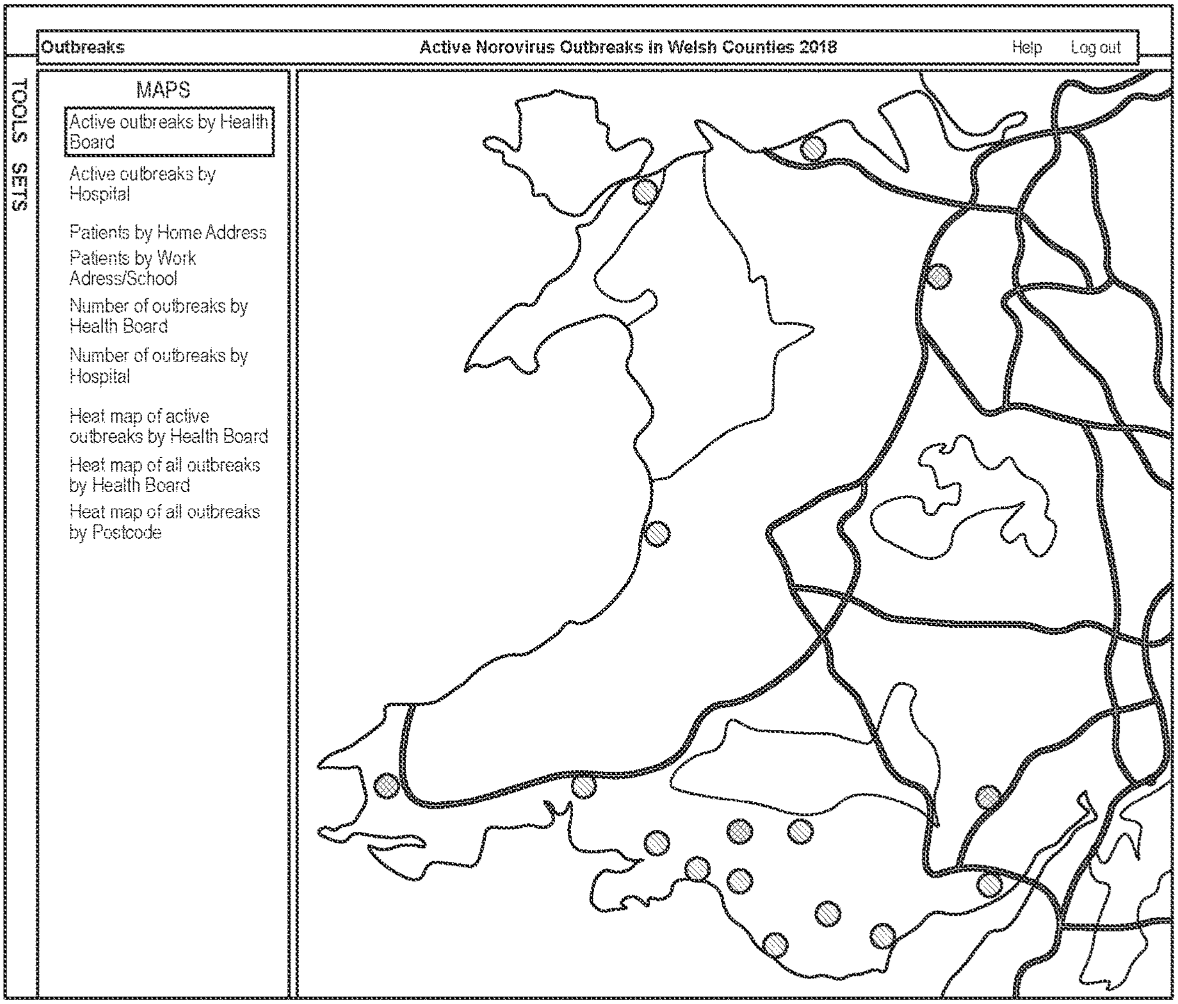

FIG. 17 illustrates a diagram of a map screen 1700 showing an outbreak of Norovirus for Welsh Counties, according to an example embodiment of the present disclosure. In the illustrated example, the database analyzer 430 receives a request to view a map of outbreaks of Norovirus for a specified location. In response, the database analyzer 430 analyzes a graph database for nodes related to Norovirus and the specified location. If a number of confirmed and/or probable cases exceeds a threshold for a particular location, the database analyzer 430 determines that an icon is to be placed on a map to indicate the presence of an outbreak in that location. In some embodiments, the threshold may be as low as one case. In some instances, the database analyzer 430 may select a color and/or size of an icon based on confirmed and/or probably cases for a particular area. A clinician may use tools with the map screen 1700 to zoom into a particular location to view, for example, individual cases by address and/or area in a medical facility. As a clinician changes a resolution of the map screen 1700, the database analyzer 430 may provide the icons at a higher resolution, such as by neighborhood, street, or residence rather than by town. To do this, the database analyzer 430 determines a scale of the displayed map, regions (e.g., neighborhoods, streets, addresses, etc.) within the display map, and confirmed and/or probable cases that correspond to the identified regions. The database analyzer 430 may also analyzer the outbreak information over time to provide an indication as to whether incidence is increasing or decreasing for a location and compare dates of incidence to determine a spread location.

Figure 18:
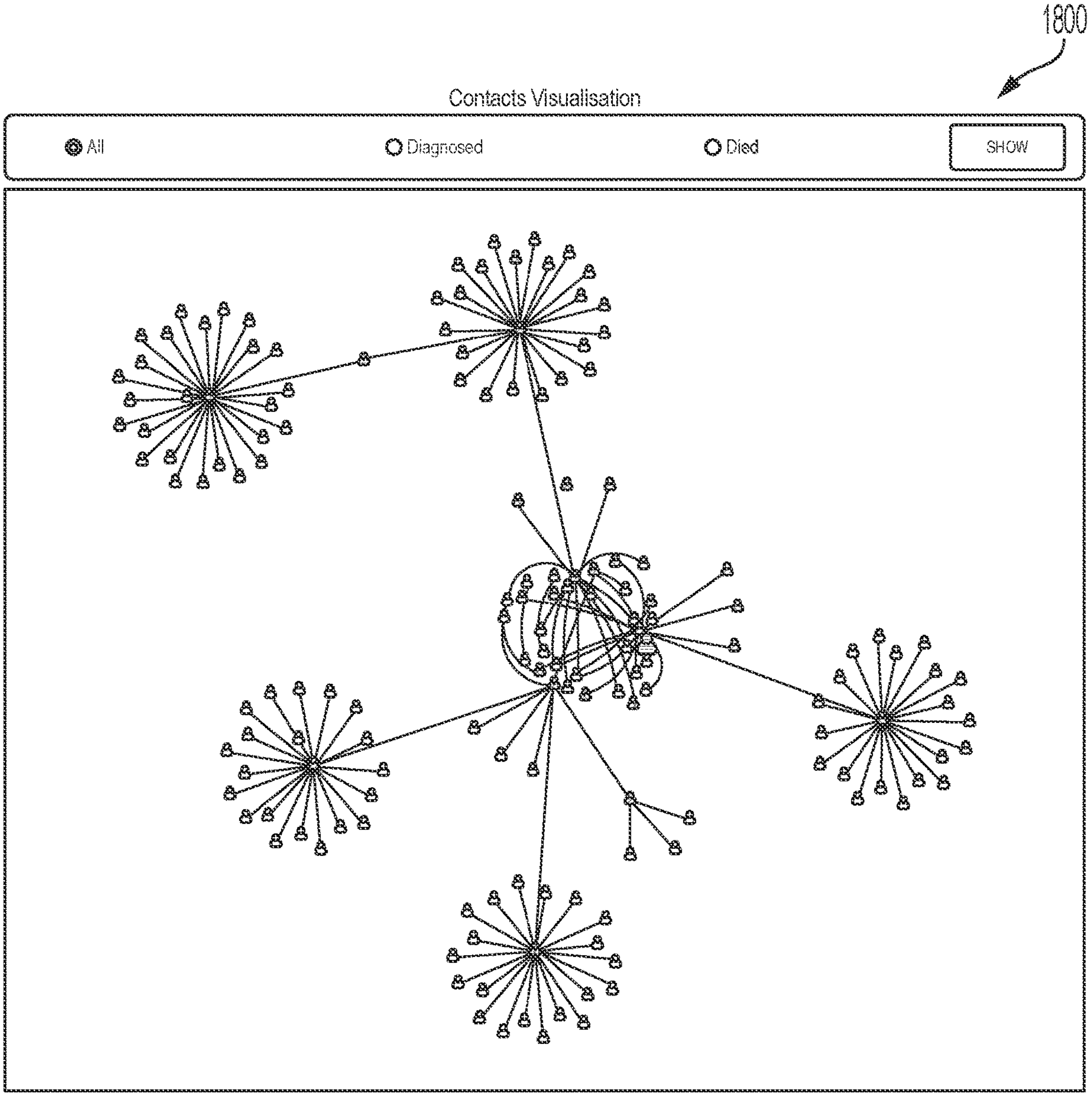

FIG. 18 illustrates a diagram of a contacts screen 1800 for an outbreak, according to an example embodiment of the present disclosure. In the illustrated example, the database analyzer 430 receives a request to view links between person hosts or nodes. The database analyzer 430 may identify confirmed, probable, or possible cases compared to all contacts for a given host. Such information may be used to quarantine or take preventive measures for certain individuals connected to an infected host. The screen 1800 may also show the interrelations among different hosts and how an outbreak is spreading.

Example Procedures for Outbreak Tracking and Management

Figure 19:
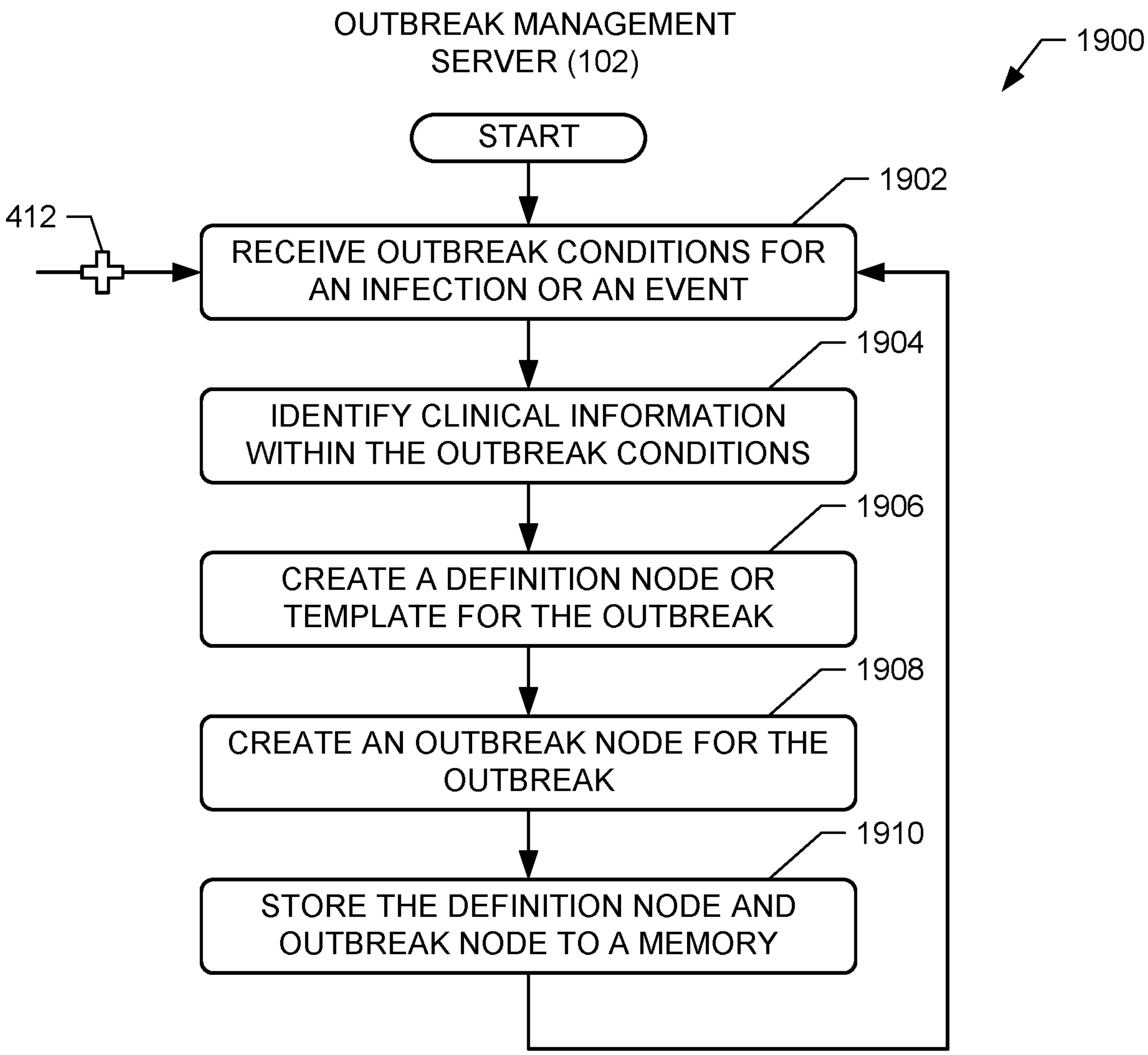
FIGS. 19 and 20 illustrate flow diagrams showing example procedures to configure and create graph databases, according to example embodiments of the present disclosure.
Figure 20:
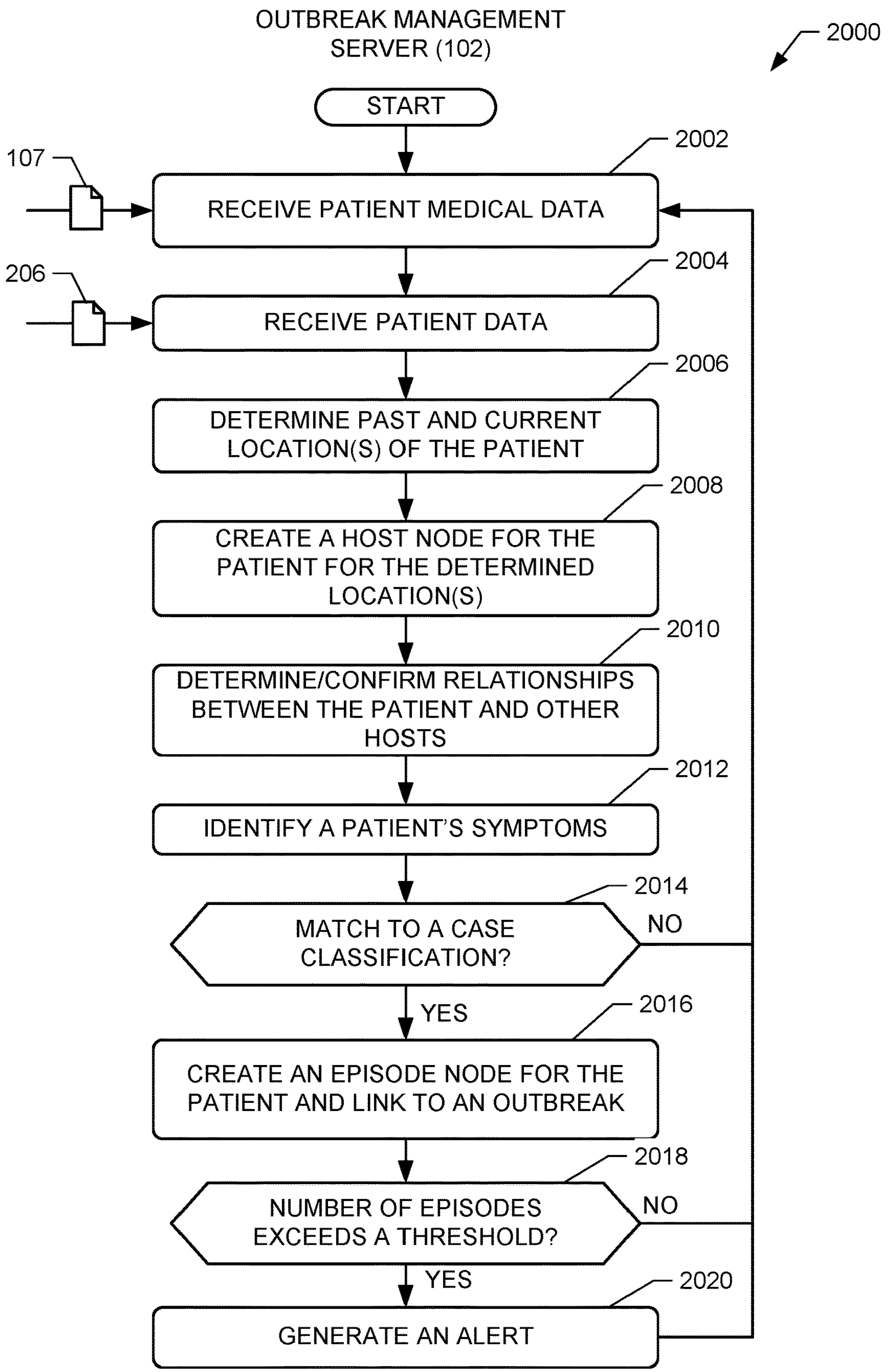

FIGS. 19 and 20 illustrate flow diagrams showing example procedures 1900 and 2000 to configure and create graphs databases, according example embodiments of the present disclosure. Although the procedures 1900 and 2000 are described with reference to the flow diagrams illustrated in FIGS. 19 and 20, it should be appreciated that many other methods of performing the steps associated with the procedures 1900 and 2000 may be used. For example, the order of many of the blocks may be changed, certain blocks may be combined with other blocks, and many of the blocks described are optional. Further, the actions described in procedures 1900 and 2000 may be performed among multiple devices including, for example the outbreak management server 102, the user device 126, the clinician device 114, the HIS 104, and/or the servers 204 of FIGS. 1 to 3. Further, the procedure may be illustrative of the instructions 128 of FIG. 4.

The example procedure 1900 of FIG. 19 begins when the outbreak management server 102 receives one or more conditions 412 for an infection or event (block 1902). The conditions 412 may be received in a document, from a website, and/or entered by a clinician. The server 102 identifies clinical information within the outbreak conditions and creates a definition node, template, and/or file for the specified outbreak (blocks 1904 and 1906). As described above in regard to FIG. 4, this includes identifying case criteria and populating the criteria into parameters or attributes of a Definition Node for the outbreak. The server 102 may also create an outbreak node that is linked to the definition node (block 1908). The server 102 stores the definition node and the outbreak node to a memory (block 1910). The case criteria for the outbreak may then be used to determine if a host has an episode within the new outbreak. If so, the outbreak may be created in a new graph database or added to a current graph database for a corresponding location.

The example procedure 2000 of FIG. 20 begins when the outbreak management server 102 receives patient medical data 107 from the HIS 104 (block 2002). The outbreak management server 102 may also receive patient data 206 from the servers 204 (block 2004). The outbreak management server 102 then determines past and current locations of the patient (or person) based on the data 107 and/or 206 (block 2006). The outbreak management server 102 creates a Host Node and Location Nodes (and Stay Nodes) for the patient/person (block 2008). The outbreak management server 102 also determines relationships between the patient and other hosts (block 2010). The determined relationships are added to the graph database between the appropriate nodes. In some examples, the outbreak management server 102 may prompt a clinician to provide the relationships with other hosts or provide a confirmation of a potential determined relationship.

The example outbreak management server 102 also identifies a patient's symptoms from the data 107 and/or 206 (block 2012). From the identified symptoms, the outbreak management server 102 determines if the patient's symptoms match a case classification for one or more outbreaks (block 2014). If there is a match to an outbreak, the outbreak management server 102 creates an Episode Node and creates a link between the patient and the outbreak (block 2016). If there is not a match to a case classification, the outbreak management server 102 returns to block 2002 and receives data for the same patient or additional patients.

If the outbreak management server 102 creates an Episode Node, the server 102 may then compare the number of patient episodes (with the same or similar Episode Nodes) to a threshold to determine if an alert should be generated or the outbreak should otherwise be promoted for further attention (block 2018). If the threshold is exceeded, the management server 102 is configured to generate an alert or otherwise transmit a message or provide an indication that the outbreak should receive attention (block 2020). This may include, for example, the server 102 transmitting one or more text messages or push notifications to clinician devices 114. If the threshold is not exceeded and/or after an alert is generated, the outbreak management server 102 returns to block 2002 for processing newly received data for the same patient or other patients.

CONCLUSION

It will be appreciated that all of the disclosed methods and procedures described herein can be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

It should be appreciated that 35 U.S.C. 112(f) or pre-AIA 35 U.S.C 112, paragraph 6 is not intended to be invoked unless the terms “means” or “step” are explicitly recited in the claims. Accordingly, the claims are not meant to be limited to the corresponding structure, material, or actions described in the specification or equivalents thereof.

The invention is claimed as follows:

1. An outbreak management apparatus comprising:

a node processor;

an outbreak tracking graph database for a disease including:

an outbreak node connected to a definition node via a ‘defined as’ link, the definition node specifying disease parameters of the disease, an episode node connected to the outbreak node via a ‘part of’ link to indicate an occurrence of the disease, and a host node associated with host parameters, the host node indicative of a patient that is associated with the outbreak node based on patient data associated with the patient matching at least some of the disease parameters, the host node connected to the episode node via a ‘part of’ link to indicate that a host has become part of an outbreak of the disease; and a memory device storing machine-readable instructions, which when executed by the node processor, cause the node processor to:

receive location data or determine location data is included within the patient data, create a stay node that is linked to the host node via a stayed link, the stay node associated with stay parameters that specify a date and/or time that the host node was at a particular location, and create a location node that is linked to the stay node via an ‘in’ link, the location node associated with location parameters that specify the particular location, determine other patients as potential hosts that were within proximity of the particular location during the date and/or time using the outbreak tracking graph database, and display information indicative of the potential hosts.

2. The outbreak management apparatus of claim 1, wherein the stay parameters additionally include start and end dates during which the host was at the particular location.

3. The outbreak management apparatus of claim 1, wherein the particular location includes at least one of a hospital bed identifier or node, a room identifier or node, a corridor identifier or node, a ward identifier or node, a level identifier or node, a wing identifier or node, a hospital identifier or node, a structure identifier or node, a building identifier or node, a street identifier or node, a site identifier or node, an area identifier or node, a state identifier or node, a country identifier or node, or GPS coordinates.

4. The outbreak management apparatus of claim 1, wherein the node processor receives the location data via a user interface.

5. The outbreak management apparatus of claim 1, wherein the disease parameters include conditions for disease classification including a ‘possible’ classification for the disease, a ‘probable’ classification for the disease, and a ‘confirmed’ classification for the disease.

6. The outbreak management apparatus of claim 1, wherein the node processor is configured to receive the patient data from at least one of an Electronic Medical Record (“EMR”) server or a third-party server, and wherein the patient data includes at least one of patient medical data, social media data, the location data, or demographic data.

7. The outbreak management apparatus of claim 1, wherein the node processor is further configured to:

determine a physical or relative distance between the patient and each of the other patients using the outbreak tracking graph database;

determine a risk score for each of the other patients based on the determined physical or relative distance; and determine which of the other patients are potential hosts based on the determined risk scores.

8. The outbreak management apparatus of claim 7, wherein the node processor is further configured to additionally determine the risk score for each of the other patients based on an amount of time the respective patient was in proximity to the host.

9. The outbreak management apparatus of claim 1, wherein the displayed information includes indications of the other patients and their proximity to the patient at the particular location.

10. The outbreak management apparatus of claim 9, wherein the displayed information is provided on a map interface.

11. The outbreak management apparatus of claim 1, wherein the node processor is further configured to transmit an alert indicative of the displayed information, wherein the alert includes at least one text message or push notification that is transmitted to at least one clinician device.

12. An outbreak management apparatus comprising:

a node processor;

an outbreak tracking graph database for a disease including:

an outbreak node connected to a definition node via a ‘defined as’ link, the definition node specifying disease parameters of the disease, an episode node connected to the outbreak node via a ‘part of’ link to indicate an occurrence of the disease, and a host node associated with host parameters, the host node indicative of a patient that is associated with the outbreak node based on patient data associated with the patient matching at least some of the disease parameters, the host node connected to the episode node via a ‘part of’ link to indicate that a host has become part of an outbreak of the disease; and a memory device storing machine-readable instructions, which when executed by the node processor, cause the node processor to:

receive location data or determine location data is included within the patient data, create stay nodes that are linked to the host node via respective stayed links, each of the stay nodes associated with stay parameters that specify a date and/or time that the host node was at a particular location, and create a separate location node that is linked to each of the stay nodes via an 'in' link, the location node associated with location parameters that specify the particular location, and display information indicative of the particular locations and indications of the dates and/or times that the patient was at the particular locations.

13. The outbreak management apparatus of claim 12, wherein the stay parameters additionally include start and end dates during which the host was at the particular location.

14. The outbreak management apparatus of claim 12, wherein the particular location includes at least one of a hospital bed identifier or node, a room identifier or node, a corridor identifier or node, a ward identifier or node, a level identifier or node, a wing identifier or node, a hospital identifier or node, a structure identifier or node, a building identifier or node, a street identifier or node, a site identifier or node, an area identifier or node, a state identifier or node, a country identifier or node, or GPS coordinates.

15. The outbreak management apparatus of claim 12, wherein the node processor receives the location data via a user interface.

16. The outbreak management apparatus of claim 12, wherein the node processor is configured to receive the patient data from at least one of an Electronic Medical Record ("EMR") server or a third-party server, and wherein the patient data includes at least one of patient medical data, social media data, the location data, or demographic data.

17. The outbreak management apparatus of claim 12, the node processor provides the displayed information in conjunction with a map interface.

18. The outbreak management apparatus of claim 12, wherein the node processor is further configured to transmit an alert indicative of the displayed information, wherein the alert includes at least one text message or push notification that is transmitted to at least one clinician device.

19. The outbreak management apparatus of claim 12, wherein the node processor is further configured to:

determine other patients as potential hosts that were within proximity of the particular locations during the specified dates and/or times using the outbreak tracking graph database; and display second information indicative of the potential hosts.

20. The outbreak management apparatus of claim 19, wherein the node processor is further configured to:

determine physical or relative distances between the patient and each of the other patients using the outbreak tracking graph database;

determine a risk score for each of the other patients based on the determined physical or relative distances; and determine which of the other patients are potential hosts based on the determined risk scores.

* * * * *